United States Patent [19]

Tanaka et al.

[11] Patent Number: 5,298,482
[45] Date of Patent: Mar. 29, 1994

[54] METHOD FOR PROMOTING PLANT GROWTH USING 5-AMINOLEVULINIC ACID OR A SALT THEREOF

[75] Inventors: Tohru Tanaka; Kiyoshi Takahashi; Yasushi Hotta, all of Saitama; Yasutomo Takeuchi; Makoto Konnai, both of Tochigi, all of Japan

[73] Assignee: Cosmo Research Institute, Tokyo, Japan

[21] Appl. No.: 881,705

[22] Filed: May 12, 1992

[30] Foreign Application Priority Data

May 14, 1991 [JP] Japan .................................. 3-107987

[51] Int. Cl.$^5$ ............................................ A01N 37/44
[52] U.S. Cl. ..................... 504/320; 504/147; 504/129; 504/130; 504/142; 504/140
[58] Field of Search .................... 71/113, 77; 504/320, 504/147, 129, 130, 142, 140

[56] References Cited

U.S. PATENT DOCUMENTS 2,395,446  2/1946  Benson ................................ 71/113

FOREIGN PATENT DOCUMENTS 8600785  2/1986  PCT Int'l Appl. .
9011013  10/1990 PCT Int'l Appl. .

OTHER PUBLICATIONS

Adamson et al, CA 103: 120098e, "Light Independent Accumulation of Chlorophyll . . . ", p. 431 (1985), (Abstract Only).
Shlyk et al, CA 84: 69771d, "Effect of 5-Amionlevulinic Acid on the Accumulation . . . ", (1976), (Abstract Only).
Chemical Abstracts, vol. 81, No. 5, Abstract No. 22178P Aug. 5, 1974.
Derwent Abstract of JP-A-01 148 193, Section Ch, AN 89-210659/29, Sep. 13, 1989.
Chemical Abstracts, vol. 78, No. 5, Abstract No. 24609S, Feb. 5, 1973.
Biological Abstracts, vol. 89, No. 1, Abstract No. 8458, Jan. 1, 1990.
Chemical Abstracts, vol. 108, No. 9, Abstract No. 70580M, Feb. 29, 1988.
Chemical Abstracts, vol. 114, No. 11, Abstract No. 98450S, Mar. 18, 1991.
Biological Abstracts, vol. 65, Abstract No. 4597 Jan. 1, 1978.
Biological Abstracts, vol. 77, No. 4, Abstract No. 30758, 1984.

Primary Examiner—Allen J. Robinson
Assistant Examiner—B. Bembenick
Attorney, Agent, or Firm—Sughrue, Mion, Zinn, Macpeak & Seas

[57] ABSTRACT

A method for treating plants with a plant growth promoter comprising 5-aminolevulinic acid or a salt thereof as an active ingredient. This treatment method is effective in enhancing the photosynthetic activity of a plant, enhancing its ability to absorb $CO_2$, suppressing its respiration, increasing its chlorophyll content and promoting its growth. As a result, the treatment greatly contributes to the promotion of rooting, the reduction of lodging, an increase in yield, an improvement in cold resistance, maintenance of freshness, an improvement and maintenance of green color, the growth of good seedlings, the promotion of organs, an increase in tillers, a shortening of the time required for growth, a relief of chemical damage and an increase in the rooting ratio in, for example, cutting.

29 Claims, No Drawings

METHOD FOR PROMOTING PLANT GROWTH USING 5-AMINOLEVULINIC ACID OR A SALT THEREOF

FIELD OF THE INVENTION

This invention relates to a method for promoting plant growth. More particularly, it relates to a novel method for promoting plant growth which is effective in, for example, promoting rooting, reducing lodging, increasing yield, improving cold resistance, maintaining freshness, improving and maintaining green color, growing good seedlings, promoting the growth of organs, increasing the number of tillers, shortening the growth period, relieving chemical damage and increasing the rooting ratio in cutting.

BACKGROUND OF THE INVENTION

A number of attempts have been made in order to improve the yield of plants. Among them, studies on plant growth regulators have been rapidly developed in recent years since plant hormones, which are physiologically active substances in common to all plants, were discovered. Six plant hormones, namely, gibberellin, auxin, cytokinin, ethylene, abscisic acid and brassinolide are known at present.

However these plant hormones mainly affect only a part of a plant organ. For example, indoleactic acid promotes rooting, gibberellin is usable in the formation of seedless grapes, ethephon promotes maturing of fruits and maleic hydrazide is usable as a sucker inhibitor for tobacco. Thus, none of them affects the whole plant or increases its yield.

On the other hand, chemicals improving the photosynthetic capability of a plant have attracted public attention since they affect the whole plant and thus increase its yield. For example, it has been found that N-allyl-N-methylglycine and N,N-dimethylglycine improve the photosynthetic capability in cultured cells (refer to Proceedings of Society of Plant Chemical Regulation in 1990). It is known, further, that choline chloride and its derivatives improve photosynthetic capability, though this function is still unsatisfactory.

SUMMARY OF THE INVENTION

It is an object of the present invention to provide a method for promoting plant growth whereby the whole plant is affected and thus, for example, its yield is increased.

Under these circumstances, the present inventors have conducted extensive studies and, as a result, found out that 5-aminolevulinic acid or its salts, the herbicidal and insecticidal actions of which have been known (refer to JP-W-61-502814 and JP-A-2-138201, the term "JP-W" as used herein means an "unexamined published Japanese international patent application" and the term "JP-A" as used herein means an "unexamined published Japanese patent application"), are unexpectedly effective in improving photosynthetic capability, suppressing respiration, improving $CO_2$ absorbing ability, increasing the chlorophyll content and promoting the growth of plants, thus achieving the above-mentioned object.

Accordingly, the present invention provides a method for promoting plant growth which comprises applying 5-aminolevulinic acid or its salt, as an active ingredient, in an effective dose to a plant to thereby achieve the effects later discussed.

DETAILED DESCRIPTION OF THE INVENTION

It is known that 5-aminolevulinic acid or its salts used in the present invention are useful as herbicides and insecticides. However it has never been reported hitherto that these compounds have a function of promoting plant growth.

5-aminolevulinic acid or its salts are known compounds and can be obtained through, for example, chemical synthesis, production by microorganisms or enzymatic production. When these compounds are produced using microorganisms or enzymes, the obtained products can be used as such without separating or purifying, so long as they are free from substances toxic to plants.

Examples of the salts of 5-aminolevulinic acid include acid addition salts such as the hydrochloride, phosphate, nitrate, sulfate, acetate, propionate, butyrate, valerate, citrate, fumarate, maleate and malate salts as well as metal salts such as the sodium salt, potassium salt and calcium salt.

These salts are employed in the form of an aqueous solution at use and thus exert the same effects as those achieved by using 5-aminolevulinic acid. Either 5-aminolevulinic acid or its salts or a mixture thereof may be used. Since 5-amionolevulinic acid or its salts is easily soluble in water, the concentration of the aqueous 5-aminolevulinic acid solution can be freely selected depending on the purpose of its actual use.

The treatment agent to be used in the method for promoting plant growth according to the present invention, which will be referred to as "the invention agent" hereinafter, may comprise 5-aminolevulinic acid or its salt alone. Alternately, it may comprise other plant growth regulators, sugars, amino acids, organic acids, alcohols, vitamins, minerals and others. Examples of the plant growth regulators usable here include brassinolides such as epibrassinolides, cholines such as choline chloride and choline nitrate, indolebutyric acid preparations, indoleacetic acid preparations, ethychlozate preparations, 1-naphthylamide preparations, isoprothiolane preparations, nicotinic acid amide preparations, hydroxyisoxasole preparations, calcium peroxide preparations, benzylaminopurine preparations, methasulfocarb preparations, oxyethylene docosanol preparations, ethephon preparations, cloxyfonac preparations, gibberellin, streptomycin preparations, daminozide preparations, 4-CPA preparations, ancymidol preparations, inabenfide preparations, uniconazole preparations, chlormequat preparations, dikegulac preparations, daminozide preparations, mefluidide preparations, calcium carbonate preparations and piperonyl butoxide preparations. Among them, brassinolides, cholines, isoprothiolane preparations, and hydroxyisoxasole preparations are preferred.

Examples of the sugars usable here include glucose, sucrose, xylitol, sorbitol, galactose, xylose, mannose, arabinose, madulose, ribose, rhamnose, fructose, maltose, lactose and maltotriose. Among them, glucose, sucrose, and galactose are preferred.

Examples of the amino acids usable here include asparagine, glutamine, histidine, tyrosine, glycine, arginine, alanine, tryptophan, methionine, valine, proline, leucine, lysine and isoleucine.

Examples of the organic acids usable here include formic acid, acetic acid, propionic acid, butyric acid, valeric acid, oxalic acid, phthalic acid, benzoic acid, lactic acid, citric acid, tartaric acid, malonic acid, malic acid, succinic acid, glycolic acid, glutamic acid, aspartic acid, maleic acid, caproic acid, caprylic acid, myristic acid, stearic acid, palmitic acid, pyruvic acid, α-ketoglutaric acid and levulinic acid. Among them, acetic acid, propionic acid, malic acid, succinic acid, glutamic acid, and levulinic acid are preferred.

Examples of the alcohols usable herein include methanol, ethanol, propanol, butanol, pentanol, hexanol and glycerol with methanol and ethanol being preferred.

Examples of the vitamins usable herein include nicotinic acid amide, vitamin $B_6$, vitamin $B_{12}$, vitamin $B_5$, vitamin C, vitamin $B_{13}$, vitamin $B_1$, vitamin $B_3$, vitamin $B_2$, vitamin $K_3$, vitamin A, vitamin $D_2$, vitamin $D_3$, vitamin $K_1$, α-tocopherol, β-tocopherol, γ-tocopherol, δ-tocopherol, p-hydroxybenzoic acid, biotin, folic acid, nicotinic acid, pantothenic acid and α-liponic acid.

Examples of the minerals usable here include nitrogen, phosphorus, potassium, boron, manganese, zinc, copper, iron, molybdenum and magnesium.

The agent to be used in the method for promoting plant growth of the present invention may be in the form of, for example, powder, granules or liquid. These formulations may be produced by a conventional method with the use of, for example, solvents, dispersion media or extenders.

The agent to be used in the method for promoting plant growth of the present invention may be in the form of either a foliage treatment agent or a soil treatment agent. Alternately, it may be absorbed by plants before planting or cutting (i.e., a soaking treatment agent). Alternately, it may be added to water for hydroponic use.

When the agent of the invention is used in foliage treatment, it preferably contains from 1 to 1,000 ppm, still preferably from 10 to 500 ppm, more preferably from 10 to 250 ppm, of 5-aminolevulinic acid or its salt and is applied in an amount of from 10 to 1,000 l, still preferably from 50 to 300 l, per 10 a ("a" means the area of 100 $m^2$). When this agent is to be applied to a plant on the leaves of which chemicals would hardly stick (for example, monocotyledon), it is desirable to further use a spreader (for example, anionic, cationic or nonionic surfactants) therewith. The type and amount of the spreader are not particularly restricted.

When the agent of the invention is used in soil treatment, it is preferably applied in an amount of from 1 to 1,000 g, still preferably from 10 to 500 g, of 5-aminolevulinic acid or its salt per 10 a. In the case of hydroponics, the agent may be used at essentially the same amount.

When the agent of the invention is used in soaking treatment whereby 5-aminolevulinic acid or its salt is absorbed by a plant before planting, the concentration of 5-aminolevulinic acid or its salt in the soaking solution preferably ranges from 0.001 to 10 ppm, still preferably from 0.01 to 5 ppm. The soaking may be carried out for 1 hour to 1 week, preferably for 3 hours to 1 day at ambient.

Although each of these treatments may be performed at any stage of the growth of a plant, it is particularly effective to perform the treatment at the seedling stage or the grain maturing stage. A single application can achieve satisfactory results. However the results can be further improved by repeating the application. When the application is to be performed twice or more, the treatment methods as described above may be appropriately combined with each other, if required. When the agent of the invention is used together with other chemicals or fertilizers in order to facilitate the application, it may be mixed with any materials so long as the effects thereof are not deteriorated thereby.

The plants to be treated with the agent of the invention are not particularly restricted. Examples thereof include cereals such as rice, barley, wheat, corn, barnyard millet and foxtail millet; vegetables such as pumpkin, turnip, cabbage, radish, Chinese cabbage, spinach, pimento and tomato; fruit trees such as orange, apple, persimmon, Japanese apricot, pear, grape and peach; flowers such as chrysanthemum, Transvaal daisy, pansy, orchid, peony and tulip; trees such as azalea, oak (*Quercus acutissima*), Japanese cedar, white cedar, Japanese oak and beech; beans such as adzuki bean, kidney bean, soybean, peanut, broad bean and pea; lawn grasses such as Korean lawn grass, bent grass and field grass; potatoes such as potato, sweet potato, Japanese taro, yam and taro; onions such as Welsh onion, onion and scallion; and pasture grasses such as alfalfa, clover and Chinese milk vetch.

The agent of the invention can be applied for, e.g., promoting rooting, reducing lodging, increasing yield, improving cold resistance, maintaining freshness, improving and maintaining green color, growing good seedlings (having thick stemmed, well colored, well rooted, but before much growth), promoting the growth of organs (e.g., root, stem, leaf, callus, shoot primordium, hairly root), increasing number of tillers, shortening the plant growth period, relieving chemical damage and increasing the rooting ratio (a ratio of the number of active rootings to the number of total treated rootings) in cutting, herbaceous cutting, foliate cutting, fix planting of seedlings, transplanting and grafting.

Next, the methods for using the agent of the invention depending on purposes and plants to be treated therewith will be described in detail.

When the agent of the invention is to be used in order to promote rooting of plants, it may be applied either by the foliage treatment, the soil treatment or by the soaking treatment, each as described above. The agent of the invention is characterized in that it can promote rooting even by the foliage treatment. In order to promote rooting, the invention agent is applicable to any plant having roots. Particularly preferable examples of plants to be treated therewith include Japanese cedar, white cedar, tea plant, mulberry, Japanese holly, seseli, kinpouju, rhododendron, doudantsutsuji (*Enkianthus perulatus*), Himalayan cedar, carnation, chrysanthemum, tulip, lawn grass, rice, camellia, mametsuge (*Buxus microphylla*), sweet osmanthus, metasequoia, spindle tree, aucuba, daphne, geranium, tobacco, dahlia, rose, orchid, pine tree, maple tree, oak, eggplant, cucumber, tomato, lettuce and cabbage. It is particularly desirable to apply the invention agent in the growth stages (for example, seedling stage) of plants, though the application time is not restricted thereto.

In order to increase the rooting ratio of plants, the invention agent may be applied either by the soil treatment, the foliage treatment or the soaking treatment, each as described above. Examples of plants to be treated with the invention agent for this purpose include seedlings of Japanese cedar, tea, rice, white cedar, pine, eggplant, cucumber, cabbage, chrysanthemum and sweet potato.

In order to grow good seedlings, the invention agent may be applied either by the soil treatment, the foliage treatment or the soaking treatment, each as described above. It is also possible to soak seeds in a solution of the invention agent (soaking treatment). The concentration of the invention agent in this soaking treatment and the soaking time may be determined in accordance with the conditions selected for soaking seedlings. Examples of plants to be treated with the invention agent for this purpose include rice, Japanese cedar, tea, white cedar, pine, eggplant, cucumber, cabbage, pimento, green pepper, okra and corn. When the invention agent is used for growing good seedlings, it may be employed together with other agents for this purpose. Examples of the other agents include isoprothiolane preparations, calcium peroxide preparations, nicotinic acid amide preparations, hydroxyisoxazole preparations, benzylaminopurine preparations and methasulfocarb preparations.

In order to reduce lodging of plants, the invention agent may be used by any method without restriction. When it is applied in the growth stage of a plant, the roots and stem of the plant grow well and, therefore, lodging can be effectively reduced in particular. Many plant growth regulators would promote the growth of plants but simultaneously cause spindly growth thereof. In contrast, the invention agent never cause any undesired spindly growth. Although the invention agent exerts satisfactory effects when used alone, these effects can be further enhanced by combining it together with an agent capable of controlling inter-node growth of plants. Examples of the agent to be combined therewith include ancymidol preparations, inabenfide preparations, uniconazole preparations, chlormequat preparations, dikegulac preparations, daminozide preparations and mefluidide preparations. Examples of plants to be treated with the invention agent for this purpose include chrysanthemum, lily, poinsettia, tulip, rice, rhododendron, rosebay, wheat, hibiscus, barley, Japanese holly, seseli, cherry tree, ibotanoki (*Ligustrum obtusifolium*), abelia and corn.

In order to increase the yield of the whole or a part of a plant, the invention agent may be used by any method and at any stage without restriction. It is particularly preferable to apply the invention agent at the early grain maturing stage. More concretely, it is particularly effective to apply the invention agent to cereals (for example, rice or wheat) before or during the blooming stage, to onions (for example, onion or garlic) at the bulb formation stage, to potatoes (for example, sweet potato or potato) at the potato formation stage, to cabbage and lettuce at the early head formation stage, and to spinach and komatsuna (*Brassica Rapa* var. *pervidis*) at the early growth stage. The invention agent is effective for increasing the yield of every plant. Namely, it is characterized by being widely applicable to, for example, cereals, potatoes, onions, beans, vegetables and fruits. In particular, the invention agent may be preferably used to increase the yields of rice, barley, wheat, sweet potato, potato, soybean, adzuki bean, kidney bean, Japanese taro, yam, onion, Welsh onion, garlic, cabbage, spinach, lettuce, komatsuna, peach, persimmon, grape, fig, kiwi, apple, banana, pineapple, tomato, eggplant, pimento, green pepper, okra, pumpkin, strawberry, asparagus, radish, carrot, broccoli, cauliflower, burdock and lotus root. Furthermore, the invention agent may be combined with, for example, cholines or brassinolides.

In order to improve the cold resistance of plants, though the invention agent may be used by any method and at any stage without restriction, it is preferred to use at the growth stage. The application of the invention agent makes it possible to enrich a plant, to improve its cold resistance and thus to accelerate the recovery of the plant from cold summer damage. Examples of plants to be preferably treated with the invention agent in order to improve cold resistance include rice, barley, wheat, corn, spinach, komatsuna, lettuce, cabbage lettuce and cabbage.

In order to maintain the freshness of plants, the invention agent may be applied either before or after harvesting. For pre-harvest application, either foliage treatment or soil treatment may be selected. It is preferable to perform the treatment within 2 weeks, still preferably within 1 week, before harvesting. As post-harvest application, foliage treatment is mainly selected. In the case of cut flowers or soaking treatment, the above-mentioned soaking treatment may be performed. This treatment is more suitable for vegetables and cut flowers, rather than fruits. Examples of plants to be treated for this purpose, include spinach, komatsuna, rape, field pea, leek, nozawana, hop, lettuce, cabbage lettuce, cabbage, broccoli, cauliflower, pimento, Welsh onion, kidney bean, chrysanthemum, carnation, freesia, Transvaal daisy, kinpouju, stock, lily, gentian and hyacinth.

In order to improve and maintain the green color of plants, the invention agent may be applied by any method and at any stage without restriction. It may be applied not only during the growth of plants but also to harvested plants. As the post-harvest application, foliage treatment is mainly selected. In the case of cut flowers or soaking treatment, the above-mentioned soaking treatment may be performed. Examples of plants to be treated therewith for this purpose include hepatica, lawn grass, spinach, komatsuna, rape, field pea, leek, hop, lettuce, cabbage lettuce, cabbage, broccoli, pimento, Welsh onion, kidney bean, chrysanthemum, carnation, freesia, Transvaal daisy, adiantum, Chinese cabbage, orchid, pothos, horutonoki (*Elaeocarpus decipiens*), agave and aloe.

In order to relieve chemical damage, the invention agent may be applied by any method at any stage without restriction. However it is recommended to apply the agent before the application of chemicals causing the damage. The invention agent is effective in promoting the whole plant and to improve its vitality so as to relieve all chemical damage. In particular, it is effective in relieving chemical damage caused by herbicides of the photosynthesis-inhibition type. In this case, it is sometimes observed that the treatment with the invention agent, even if performed after the application of the herbicide causing the chemical damage, promotes recovery. Examples of herbicides of this type include pyrazolate preparations, dimethazone preparations, chlorphthalim preparations, oxadiazone preparations, phthalimide preparations, fluridone preparations, dicyanomalelonitrile preparations, carbamate preparations, urea preparations and triazine preparations. In addition, the invention agent is highly effective in relieving chemical damage caused by organic phosphoric acid insecticides (e.g., diazinon, sulprofos) and carbamate insecticides (e.g. 1-naphtylmethylcarbamate, methomyl).

In order to increase the number of tillers, the invention agent may be applied by any method at any stage without restriction. Namely, it is usable in seed treatment (soaking treatment), soil treatment or foliage or soil treatment after planting. Examples of plants to be preferably treated therewith for this purpose include cereals such as rice and barley.

In order to shorten the growth time of plants, the invention agent may be applied by any method at any stage without restriction. Namely, it is usable either in soil treatment, foliate treatment or soaking treatment. Examples of plants preferably treated therewith for this purpose include cereals such as rice and barley, various vegetables and fruit trees. In particular, the growth time of plants frequently suffering from cold summer damage can be shortened by using the invention agent and, as a result, cold summer damage can be prevented.

In order to promote the growth of organs, it is preferable to add the invention agent to a medium (for example, a Murashige-Skoog medium, a Linsmaier-Skoog medium) during the incubation of said organ. Similar to the above-mentioned soaking treatment, the concentration of the invenlion agent preferably ranges from 0.001 to 10 ppm, still preferably from 0.01 to 5 ppm, and the incubation may be performed at 20° to 30° C., preferably 25° C. for from 1 hour to 1 week, preferably from 3 hours to 1 day. Other conditions (e.g., quantity of light, amount of airflow) are dependent on a plant. Examples of the organ include callus, shoot primordium, hairly root, stem, hypocotyl, root, and pollen.

Although the function mechanism of the agent used in the method for promoting plant growth of the present invention has never been clarified in detail, it is assumed that the photosynthetic activity and $CO_2$ absorption capability are enhanced, respiration is suppressed and the chlorophyll content is increased. That is to say, the application of the invention agent: (1) enhances photosynthetic activity; (2) increases chlorophyll content; and (3) enhances $CO_2$ absorption capability. The photosynthetic activity is determined by the $CO_2$ fixing amount by photosynthesis of a plant. The chlorophyll content is a total amount of the chlorophyll of a reaction center and the light collective chlorophyll. The $CO_2$ absorption capability is determined by the difference in $CO_2$ absorption amount of photosynthesis and breathing of a plant. A plant fixes $CO_2$ by photosynthesis while metabolizing the photosynthetic products by respiration, thus liberating $CO_2$. When the invention agent is applied to the plant, respiration is suppressed and thus the accumulation of the photosynthetic products is accelerated. The amount of respiration is the $CO_2$ amount by respiration of a plant. It is therefore considered that the growth of the plant is promoted through the above-mentioned three functions.

When applied to plants, 5-aminolevulinic acid or its salt would enhance the photosynthetic activity and the $CO_2$ absorption capability, suppress the respiration and increase the chlorophyll content. Thus the method of the present invention is highly effective in, for example, promoting rooting, reducing lodging, increasing yield, improving cold resistance, maintaining freshness, improving and maintaining green color, growing good seedlings, promoting the growth of organs, increasing the number of tillers, shortening the growth period, relieving chemical damage and increasing the rooting ratio in cutting.

To further illustrate the present invention in greater detail, and not by way of limitation, the following Examples will be given. Unless otherwise indicated, all Examples were conducted at room temperature. In addition, % is indicated by % by weight based on the total solution amount.

EXAMPLE 1

Cucumber (aonaga-jibae) seeds were pasteurized by soaking in a 2% solution of sodium hypochlorite for 10 minutes and then allowed to absorb water by washing under running water for 4 hours. Next, these seeds were sowed on moistened vermiculite and grown at 25° C. under a daylight fluorescent lamp of 6,000 lux for 6 days. The sprouts thus obtained were harvested. Then a piece was cut from each sprout 5 mm below the cotyledon nod. Six pieces were each introduced into distilled water and 1 ppm and 3 ppm aqueous solutions of 5-aminolevulinic acid (hereinafter simply referred to as 5-ALA) and incubated at 25° C. under irradiation at 6,000 lux for 20 hours. Then the length of each piece was measured. Further, the green color of each piece was evaluated in 5 grades, 1, 2, 3, 4, 5 referring to the color of the control lot (distilled water) as 3, with the naked eye. The more number means thicker green and good results. Table 1 summarizes the averages.

TABLE 1

| 5-ALA conc. | 0 ppm | 1 ppm | 3 ppm |
| --- | --- | --- | --- |
| Average (length: mm) | 5.62 | 5.84 | 5.96 |
| Standard deviation | 0.17 | 0.22 | 0.42 |
| Green color | 3 | 5 | 4 |

As the above results clearly show, the addition of 5-ALA promoted the growth and improved green color.

EXAMPLE 2

Young rice (sasanishiki) seedlings of about 8 cm in above-ground length, which had been grown in a seedling-raising box, were cut in such a manner as to give an above-ground length of 5 mm and sowed in high-wall Petri dishes in such a manner that each dish had 10 seeds. Then a 5-ALA aqueous solution or a control was added to each dish so as to give a depth of 1 cm and the seedlings were grown at 25° C. under 6,000 lux for 8 days. Next, the length of regenerated leaves and the total weight thereof were measured.

Table 2 shows the average data of 10 seeds.

TABLE 2

| 5-ALA conc. | Leaf length (cm) | Total weight (mg) |
| --- | --- | --- |
| 0 ppm | 4.1 | 49.4 |
| 1 ppm | 6.8 | 64.3 |

As Table 2 clearly shows, the addition of 5-ALA promoted the growth of the regenerated leaves.

EXAMPLE 3

Young rice (sasanishiki) seedlings of about 3 cm in above-ground length, which had been grown in a seedling-raising box, were soaked in 0 ppm, 1 ppm and 3 ppm 5-ALA aqueous solutions for 1, 6, 9, 24 and 48 hours (each lot having 8 seedlings). After washing with water, these seedlings were transplanted into paddy field pots and grown in a greenhouse for 2 weeks. Then the seedlings were pulled out and the above-ground length, total weight after removing the husk, and the number of roots of each seedling were determined and the average data were calculated. Tables 3, 4 and 5 show the results.

TABLE 3

| 5-ALA conc. | Above-ground length (cm/seedling) Soaking time | | | | |
|---|---|---|---|---|---|
| (ppm) | 1 hr | 6 hr | 9 hr | 24 hr | 48 hr |
| 0 | 4.85 | 5.39 | 6.08 | 5.06 | 5.34 |
| 1 | 5.57 | 6.87 | 6.10 | 6.64 | 4.70 |
| 3 | 6.00 | 7.88 | 5.62 | 7.24 | 6.27 |

TABLE 4

| 5-ALA conc. | Total weight (mg/seedling) Soaking time | | | | |
|---|---|---|---|---|---|
| (ppm) | 1 hr | 6 hr | 9 hr | 24 hr | 48 hr |
| 0 | 21.9 | 34.3 | 32.2 | 28.8 | 26.6 |
| 1 | 38.9 | 54.3 | 47.6 | 50.4 | 36.6 |
| 3 | 45.4 | 50.8 | 35.3 | 50.8 | 44.7 |

TABLE 5

| 5-ALA conc. | No. of roots (/seedling) Soaking time | | | | |
|---|---|---|---|---|---|
| (ppm) | 1 hr | 6 hr | 9 hr | 24 hr | 48 hr |
| 0 | 3.4 | 4.1 | 2.5 | 3.4 | 3.7 |
| 1 | 4.5 | 7.0 | 4.8 | 6.2 | 4.2 |
| 3 | 5.4 | 7.2 | 5.4 | 6.6 | 6.4 |

As the above Tables 3, 4 and 5 clearly show, the treatment with the invention agent was effective in promoting the growth and the rooting, increasing the rooting ratio of rice and growing good seedlings.

EXAMPLE 4

Rice seeds (akinishiki) were pasteurized and sprouted in a conventional manner. Then seeds of uniform size were selected and sowed with a pair of tweezers on expanded polyethylene sheets channeled with a cutter at a ratio of 10 seeds per sheet. Next, these sheets were floated in high-wall Petri dishes filled with 150 ml portions of 5-ALA aqueous solutions of various concentrations. After growing at 28° C. under 5,000 lux for 7 days, the above-ground length, the longest root and the number of roots of each seedling were determined. Table 6 shows the average values of 10 seeds.

TABLE 6

| 5-ALA conc. (ppm) | Above-ground length (cm) | Longest root (cm) | No. of Roots |
|---|---|---|---|
| 0 | 6.4 | 6.8 | 4.2 |
| 0.01 | 7.5 | 8.3 | 6.2 |
| 0.03 | 7.9 | 7.0 | 8.7 |
| 0.1 | 7.8 | 7.5 | 5.5 |
| 0.3 | 6.7 | 7.3 | 4.8 |

As Table 6 clearly shows, the addition of 5-ALA resulted in the elongation of the above-ground length and the root length and increased the number of roots, which indicated that rooting was promoted and good seedlings were grown.

EXAMPLE 5

Rice seedlings (akinishiki, above-ground length: about 5 cm) grown in a seedling-raising box were cut so as to leave 5 mm of roots. Then these seedlings were introduced into flat-bottomed test tubes containing 50 ml portions of 5-ALA aqueous solutions of various concentrations and fixed with cotton plugs in such a manner that the roots came in contact with the solutions. 12 test tubes were prepared for each concentration and classified into two groups. The seedlings of one group were grown at 28° C., under irradiation at 5,000 lux for 24 hours, for 7 days [Condition A]. The test tubes of the other group were coated with an aluminum foil so as to shade the roots and the seedlings were grown, under a cyclic system of 28° C. at 5,000 lux for 12 hours and at 23° C. in the dark for 12 hours, for 7 days [Condition B]. After 7 days, the seedlings were taken out and the roots were cut. Then the total length of the roots were measured. Table 7 shows the average of 6 seedlings of each lot.

TABLE 7

| | Root Length (cm) | | |
|---|---|---|---|
| | 0 ppm | 0.01 ppm | 0.03 ppm |
| Condition A | 30.8 | 37.4 | 36.6 |
| Condition B | 35.8 | 40.8 | 40.7 |

As Table 7 clearly shows, the addition of 5-ALA promoted the growth and rooting and thus good seedlings were grown.

EXAMPLE 6

A 5-ALA containing broth was prepared using a photosynthetic bacterium with the use of anaerobically treated swine feces as a medium in accordance with the method described in detail in JP-A-2-92293 (the term "JP-A" as used herein means an "unexamined published Japanese patent application"). This broth was centrifuged at 8,000 rpm for 30 minutes to give a supernatant. The obtained supernatant contained 720 ppm of 5-ALA. Then, the procedure of Example 4 was repeated, except that this broth was diluted to give a definite 5-ALA concentration and the culture was performed for 3 days. After 3 days, the root length was measured. Table 8 shows the average value per sheet (10 seeds).

TABLE 8

| 5-ALA conc. | Average root length (cm) | | |
|---|---|---|---|
| (ppm) | Sheet 1 | Sheet 2 | Sheet 3 |
| 0 | 1.0 | 1.2 | 1.8 |
| 0.0072 | 2.1 | 2.7 | 3.1 |
| 0.036 | 2.9 | 3.0 | 3.1 |
| 0.072 | 2.6 | 3.0 | 3.2 |
| 0.72 | 2.7 | 2.9 | 3.0 |

As Table 8 clearly shows, the effects exerted by using the above-mentioned unpurified broth produced by the microorganism were comparable to those achieved by using purified products.

EXAMPLE 7

The husks of rice seedlings (akinishiki, above-ground length: about 15 cm) grown in a seedling-raising box were removed and the seedlings were cut so as to give a root length of 1 cm. Then these seedlings were introduced into 100 ml Erlenmeyer flasks containing 100 ml portions of Kasuga's solution A [pH 5.1; refer to Jikken Nogei Kagaku, II, 3rd Ed., Asakura Shoten, p. 306] containing 5-ALA at various concentrations and fixed therein. The roots were shaded with an aluminum foil. After growth at 28° C. under 5,000 lux for 7 days, the length of the regenerated root (the longest one) was measured. Table 9 shows the results.

TABLE 9

| 5-ALA conc. (ppm) | Root length (cm) | | | | |
|---|---|---|---|---|---|
| Lot No. | 0 | 0.001 | 0.01 | 0.1 | 1 |
| 1 | 3.4 | 5.1 | 6.1 | 6.8 | 6.3 |
| 2 | 4.7 | 6.1 | 6.5 | 7.0 | 6.3 |
| 3 | 4.7 | 6.6 | 7.0 | 7.6 | 6.7 |
| 4 | 4.8 | 6.7 | 8.0 | 8.6 | 7.1 |

As Table 9 clearly shows, the addition of 5-ALA promoted the growth and the rooting and thus good seedlings were grown.

EXAMPLE 8

On Jun. 22, rice seedlings (akinishiki, above-ground length: about 12 cm) grown in a seedling-raising box were transplanted in a paddy field pot of 1/2000 a, prepared by a conventional method, at a ratio of 2 seedlings in 4 points per pot.

Immediately after the transplanting, 10 g, 30 g and 100 g per 10 a of 5-ALA was applied to the soil, while an untreated lot was also prepared as a control. Then the seedlings were managed under common conditions at a water depth of about 2 cm. On Jul. 10 (i.e., 18 days after the transplantation), the soil was washed away and the above-ground length and the total dry weight of each seedling were measured. Table 10 shows the results expressed as the average per pot.

TABLE 10

| | Above-ground length (cm) | Dry weight (g) |
|---|---|---|
| Untreated | 34.2 (100) | 1.82 (100) |
| 10 g/10 a | 38.6 (113) | 2.46 (135) |
| 30 g/10 a | 39.7 (116) | 2.33 (128) |
| 100 g/10 a | 41.5 (121) | 2.76 (152) |

*: Figures given in parentheses are ratios with reference to the data of the untreated lot (%).

As Table 10 clearly shows, the treatment with 5-ALA promoted the growth. Further, the ratio of the weight gain exceeded that of the elongation in the above-ground length, which indicated that the treatment with 5-ALA did not cause spindly growth, which might result in lodging, but rather resulted in normal growth of the plants. Thus, it was found out that the invention agent contributed to the growth of good seedlings and was highly effective in practice.

EXAMPLE 9

On Jul. 17, rice seedlings (akinishiki, above-ground length: about 10 cm) grown in a seedling-raising box were transplanted in a paddy field pot of 1/2000 a, prepared by a conventional method, at a ratio of 2 seedlings in 4 points per pot.

Immediately after the transplanting, 4 ml portions of 5-ALA aqueous solutions of various concentrations, each containing the spreader neoesterin diluted to 2,000-fold (aqueous solution: spreader=2,000:1, hereinafter the same), were sprayed onto the pots (80 1/10 a). Then the seedlings were managed under common conditions at a water depth of about 2 cm. On Aug. 7 (i.e., 3 weeks after the transplantation), the soil was washed away and the above-ground length, the total dry weight and the number of tillers of each seedling were measured. Table 11 shows the results expressed as the average per pot.

TABLE 11

| 5-ALA conc. | | Above-ground length (cm) | Dry weight (g) | No. of Tillers |
|---|---|---|---|---|
| Untreated | 1 | 51.0 | 1.44 | 2.7 |
| | 2 | 47.4 | 1.53 | 3.0 |
| | 3 | 48.9 | 1.56 | 3.0 |
| | 4 | 49.9 | 1.58 | 3.0 |
| 10 ppm | 1 | 47.6 | 1.65 | 3.0 |
| | 2 | 50.5 | 1.73 | 3.2 |
| | 3 | 49.9 | 2.19 | 3.4 |
| 30 ppm | 1 | 48.8 | 2.14 | 3.2 |
| | 2 | 52.9 | 2.15 | 3.3 |
| | 3 | 50.9 | 2.16 | 3.4 |
| | 4 | 50.2 | 2.21 | 3.5 |
| 100 ppm | 1 | 51.1 | 2.05 | 3.3 |
| | 2 | 52.1 | 2.15 | 3.3 |
| | 3 | 49.6 | 2.45 | 3.5 |
| | 4 | 49.7 | 2.46 | 3.5 |

As Table 11 clearly shows, the treatment with 5-ALA promoted the growth and increased the rooting ration. Further, the dry weight and tiller number were remarkably increased, while the above-ground length showed little elongation, which indicated that the seedlings were highly resistant against lodging and high yield could be expected.

EXAMPLE 10

On Jun. 22, the roots of rice seedlings (akinishiki, above-ground length: about 12 cm) grown in a seedling-raising box were soaked in 5-ALA aqueous solutions of various concentrations for 12 hours so as to allow the seedlings to absorb the solutions. On Jun. 23, these seedlings were transplanted into the same pots as those used in the above Example 8 in the same manner and then they were managed under common conditions at a water depth of about 2 cm till Jul. 10 (namely, for 17 days). On Jul. 10, the soil was washed away and the above-ground length and total dry weight of each seedling were measured. 2 pots were employed for each concentration and thus 16 seedlings were used. Table 12 shows the results expressed in average.

TABLE 12

| 5-ALA conc. (ppm) | Above-ground length (cm) | Total dry weight (g) |
|---|---|---|
| 0 | 35.2 | 1.67 |
| 0.01 | 34.8 | 1.79 |
| 0.1 | 35.0 | 1.90 |
| 1 | 37.1 | 1.84 |
| 10 | 36.2 | 1.73 |

As Table 12 clearly shows, the treatment with 5-ALA promoted the growth and increased the rooting ratio. Further, the ratio of the weight gain exceeded that of the elongation in the above-ground length, which indicated that the treatment with 5-ALA promoted the normal growth of the plants without being accompanied by any spindly growth. Thus, it was found that the invention agent was highly effective in practice.

EXAMPLE 11

On Jun. 12, 10 radish seeds (comet, Sakata) were sowed in a 1/5000 a pot filled with field soil to which 10 kg/10 a, in terms of nitrogen, of a compound fertilizer (N:P:N=8:8:8 (wt %), the product of Nitto Hiryo Kagaku Kogyo K. K., Japan) had been applied as the basal dressing. Then, the seeds were cultured in a greenhouse. On Jun. 26 (2 to 4 true leaf stage), the seedlings were thinned while leaving 4 seedlings of uniform size per pot. A spreader neoesterin was diluted 2,000-fold with 5-ALA solutions of various concentrations. Then the seedlings were subjected to foliage treatment with 2 ml per pot of the solutions thus obtained. The seedlings were managed under common conditions till Jul. 4 and then harvested. The harvested plants were washed with water and dried in a drier at 80° C. for 24 hours, followed by weighing each seedling. Table 13 shows the results expressed in the average weight per pot.

TABLE 13

| 5-ALA conc. (ppm) | Average dry weight (g/seedling) |
| --- | --- |
| 0 | 0.97 |
| 1 | 1.04 |
| 3 | 1.17 |
| 10 | 1.17 |
| 30 | 1.36 |
| 100 | 1.34 |
| 300 | 1.26 |

As Table 13 clearly shows, the treatment with 5-ALA promoted the growth and increased the yield.

EXAMPLE 12

On Jun. 12, 10 corn seeds (honey bantam sweet corn, Sakata) were sowed in a 1/5000 a pot filled with field soil to which 10 kg/10 a, in terms of nitrogen, of a compound fertilizer had been applied as the base dressing. Then the seeds were cultured in a greenhouse. On Jun. 26 (3 to 4 leaf stage), the seedlings were thinned while leaving 7 seedlings of uniform size per pot. A spreader neoesterin was diluted 2,000-fold with 5-ALA solutions of various concentrations. Then the seedlings were subjected to foliage treatment with 2 ml per pot of the solutions thus obtained.

The seedlings were managed under common conditions. On Jul. 7, the above-ground parts were cut (5 to 6 leaf stage) and the above-ground length and the above-ground weight (wet weight) of each seedling were measured and the average values per pot were calculated. Table 14 shows the results.

TABLE 14

| 5-ALA conc. (ppm) | Average above-ground weight (g/seedling) | (%) | Average above-ground length (cm/seedling) | (%) |
| --- | --- | --- | --- | --- |
| 0 | 2.88 | (100) | 43.6 | (100) |
| 3 | 2.93 | (102) | 43.8 | (100) |
| 10 | 3.76 | (131) | 47.5 | (109) |
| 30 | 3.72 | (129) | 45.6 | (105) |
| 100 | 3.36 | (117) | 45.4 | (104) |
| 300 | 3.11 | (108) | 46.2 | (106) |

As Table 14 clearly shows, the treatment with 5-ALA promoted growth. Further, the above-ground weight gain exceeded that of the elongation in the above-ground length, which indicated that the treatment with 5-ALA promoted the normal growth of the plants without being accompanied by any spindly growth. Thus, it was found out that good seedlings highly resistant against lodging were obtained.

EXAMPLE 13

On Jul. 10, 6 soybeans (akishirome) were sowed in a 1/5000 a pot filled with field soil to which 10 kg/10 a, in terms of nitrogen, of a compound fertilizer had been applied as the basal dressing. Then, the beans were cultured in a greenhouse. On Jul. 24 (first compound leaf stage), the seedlings were thinned while leaving 3 seedlings of uniform size per pot. A spreader neoesterin was diluted 2,000-fold with 5-ALA solutions of various concentrations. Then the seedlings were subjected to foliage treatment by spraying 3 ml per pot of the solutions thus obtained thereon.

The seedlings were managed under common conditions. On Aug. 11, the soil was washed away with water and the seedlings were harvested. After measuring the above-ground length, each seedling was dried in a drier at 80° C. for 24 hours, followed by weighing. Table 15 shows the results expressed in the average data per pot.

TABLE 15

| 5-ALA conc. (ppm) | Average total weight (g/plant) | Average above-ground length (cm/plant) |
| --- | --- | --- |
| 0 | 1.68 | 37.7 |
| 10 | 1.99 | 41.4 |
| 30 | 2.13 | 42.1 |
| 100 | 1.79 | 40.6 |

As Table 15 clearly shows, the treatment with 5-ALA promoted the growth and thus good seedlings were effectively grown.

EXAMPLE 14

On Jun. 12, 8 kidney beans (Aron, Sakata) were sowed in a 1/5000 a pot filled with field soil to which 10 kg/10 a, in terms of nitrogen, of a compound fertilizer had been applied as the basal dressing. Then, the beans were cultured in a greenhouse. On Jul. 3 (first compound leaf stage), the seedlings were thinned while leaving 4 seedlings of uniform size per pot. A spreader neoesterin was diluted 2,000-fold with 5-ALA solutions of various concentrations. Then the seedlings were subjected to foliage treatment by spraying 2 ml per pot of the solutions thus obtained thereon.

The seedlings were managed under common conditions. On Jul. 17, the soil was washed away with water and the seedlings were harvested. Then, the above-ground fresh weight of each seedling was measured and the leaves were counted. Then the roots were separated from the above-ground part and dried in a drier at 80° C. for 24 hours, followed by determining the dry weight per pot. 3 pots were employed for each concentration. The above-ground weight and leaf number were expressed as an average per plant, while the dry root weight was expressed as an average value per pot. Table 16 shows the results.

TABLE 16

| 5-ALA conc. (ppm) | Average above-ground weight (g/plant) | Average number of leafs (No./plant) | Average dry root weight (g/pot) |
| --- | --- | --- | --- |
| 0 | 5.6 | 7.3 | 3.3 |
| 1 | 6.3 | 7.5 | 3.7 |
| 3 | 6.7 | 7.4 | 3.5 |
| 10 | 6.7 | 8.4 | 5.0 |
| 30 | 6.9 | 8.3 | 6.5 |
| 100 | 6.8 | 8.3 | 5.7 |
| 300 | 6.2 | 7.8 | 4.8 |

As Table 16 clearly shows, the treatment with 5-ALA promoted growth. Further, the increase in the average leaf number indicated that the growth of the plant was promoted, the time required for harvesting was shortened and the growth period was shortened.

Furthermore, the treatment with 5-ALA exerted a marked effect on the dry root weight. Thus, it was found that the invention agent was highly effective in promoting rooting, increasing the rooting ratio and in EXAMPLE 15 and COMPARATIVE EXAMPLE 1

On Aug. 24, tips of sweet potato runners each having 5 leaves were cut. From those of uniform size, 2 leaves from the bottom were removed and the stems were soaked in 5-ALA aqueous solutions of various concentrations and in a Sun-catch TM (product of Mitsubishi Gas Chemical Co., Inc.) aqueous solution adjusted to such a concentration so as to contain 20 ppm of choline chloride for 24 hours. After 24 hours (Aug. 25), these stems were vertically transplanted in deep pots No. 8 (diameter: 24 cm) filled with field soil in such a manner that the remaining 3 leaves were located above ground. Then water was sufficiently given and the plants were grown in a greenhouse for 2 weeks. On Sep. 7, the soil was washed away with water and each root thus formed was cut with a scalpel. The obtained roots were dried in a drier at 50° C. for 48 hours. 4 pots were employed for each solution and the average dry root weight of 4 stems was determined. Table 17 shows the results.

TABLE 17

| | 5-ALA conc. (ppm) | Dry root weight (g/plant) | Gain (%) |
|---|---|---|---|
| Ex. 15 | 0 | 0.42 | 100 |
| | 0.01 | 1.07 | 255 |
| | 0.1 | 0.79 | 188 |
| | 1 | 0.62 | 148 |
| | 10 | 0.51 | 121 |
| C. Ex. 1 | Sun-catch TM (20 ppm) | 0.73 | 174 |

As Table 17 clearly shows, the treatment with 5-ALA promoted growth and rooting and increased the rooting ratio. When compared with Comparative Example 1, the invention agent was twice or more as effective as Sun-catch TM, Which is a plant growth promoter known to be effective in increasing the rooting ratio of potatoes, even at a concentration as low as 1/2,000.

EXAMPLE 16

On Sep. 1, 2 ridges 1 m in width were formed on a field to which 10 kg/10 a, in terms of nitrogen, of a compound fertilizer had been applied as a basal dressing. Then two varieties of radish seeds (miyashige-sobutori, tensei-aokubi), were sowed each in 2 lines and then managed under common conditions (thinning and top dressing). On Oct. 1 (after 1 month), radish seedlings of each variety were divided into 2 groups. Then a 5-ALA (100 ppm) aqueous solution containing a spreader neoesterin diluted 2,000-fold was sprayed onto the leaves of the seedlings of one group, while a solution prepared by adding neoesterin in the same amount as described above to water was sprayed onto the seedlings of the other group, each in a dose of 1 ml per plant.

Next, the plants were managed under common conditions. On Oct. 18, the diameter of the thickest portion of the above-ground part of each radish was measured with a slide caliper.

Table 18 shows the obtained data and average values.

TABLE 18

| | Diameter (cm) | | Diameter (cm) | |
|---|---|---|---|---|
| | Miyashige treated | Miyashige untreated | Tensei treated | Tensei untreated |
| Average | 55.9 | 51.5 | 60.2 | 56.6 |
| Standard deviation | 5.4 | 5.9 | 7.5 | 9.0 |

As Table 18 clearly shows, the treatment with 5-ALA also promoted growth and increased yield in the field. Although differences in diameter were seemingly small, thickness is an important factor in the evaluation of a radish and the above differences in diameter corresponded to about 20% in radish weight. Thus, the effects achieved by the invention agent were highly useful.

EXAMPLE 17 and COMPARATIVE EXAMPLE 2

On Dec. 3, onion seedlings (SENSYUchukoudaka kitamanegi) were sealed in vinyl bags and allowed to stand in an incubator at 37° C. for 48 hours to thereby damage the seedlings. Next, the leaves were cut at 10 cm above the above-ground part. These seedlings were washed with water and the roots were soaked in 5-ALA aqueous solutions of various concentrations and in a Sun-catch TM aqueous solution adjusted so as to contain 20 ppm of choline chloride for 12 hours.

The onion seedlings thus treated were transplanted onto a ridge (width: 1 m) in a field, to which 10 kg/10 a, in terms of nitrogen, of a compound fertilizer had been applied as the basal dressing, at intervals of 25 cm in 3 lines of 15 cm in width. Then the seedlings were managed under common conditions. On Mar. 26, plants showing good growth were counted. Table 19 shows the number of planted seedlings, the number of rooting seedlings and their rooting ratios.

TABLE 19

| | 5-ALA conc. (ppm) | No. of planted seedling | No. of rooting seedling | Rooting ratio (%) |
|---|---|---|---|---|
| Ex. 17 | 0 | 38 | 5 | 13.2 |
| | 0.001 | 18 | 9 | 50.0 |
| | 0.01 | 18 | 11 | 61.1 |
| | 0.1 | 18 | 16 | 88.9 |
| | 1 | 18 | 17 | 94.4 |
| | 10 | 18 | 9 | 50.0 |
| C. Ex. 2 | Sun-catch TM (20 ppm) | 17 | 10 | 58.8 |

As Table 19 clearly shows, the treatment with 5-ALA increased the rooting ratio. It was observed that seedlings which withered without rooting were damaged by cold weather. Thus, it was found that the treatment with the invention agent could improve cold resistance. It was further found that the invention agent achieved superior effects at a lower concentration, compared with the conventional product employed in Comparative Example 2.

EXAMPLE 18 and COMPARATIVE EXAMPLE 3

On Jul. 17, 10 radish seeds (comet, Sakata) were sowed in a 1/5000 a pot filled with field soil to which 10 kg/10 a, in terms of nitrogen, of a compound fertilizer had been applied as the basal dressing. Then the seeds were cultured in a greenhouse. On Jul. 28, the seedlings were thinned while leaving 6 seedlings of uniform size per pot. On Aug. 2, 12 pots of uniform size were selected. Then the CO$_2$ absorption concentration of each pot was determined by using a photosynthetic activity determination device (product of Shimadzu Seisakusho) at 27° C., at a reference gas flow rate of 0.5 l/min, at a target gas flow rate of 0.5 l/min, at a fan rate of 8 l/min and under 70,000 lux. Simultaneously, the increase in CO$_2$ due to respiration was determined under shaded conditions. Next, a solution of a spreader neoesterin diluted 1,000-fold, solutions prepared by adding 30 ppm of 5-ALA, 100 ppm of 5-ALA and Sun-catch, Sun-catch being added in such an amount as to give 100 ppm of choline chloride, to the solution of the spreader were applied by spraying at an amount of 3 ml per pot (3 pots for each solution).

Then, the seedlings were managed under common conditions. 2 days (Aug. 4), 5 days (Aug. 7) and 9 days (Aug. 11) after the application, the CO$_2$ absorption concentration and the increase in CO$_2$ due to respiration were determined by the same method as the one performed on Aug. 2. 26 days after the application (Aug. 28), the plants were harvested, washed with water and dried in a drier at 80° C. for 24 hours. Then, the total dry weight of each plant was measured. The CO$_2$ concentration of each pot at each point was calculated by referring to the CO$_2$ concentration measured prior to the treatment on Aug. 2 as 100%, and the average of 3 pots for each condition was determined. The total dry weight was also measured in the same manner. Tables 20, 21 and 22 show the results.

TABLE 20

|  | Photosynthesis activity (CO$_2$ absorption %) | | | |
| --- | --- | --- | --- | --- |
|  | Before treatment | After 2 days | After 5 days | After 9 days |
| Ex. 18 |  |  |  |  |
| spreader alone | 100 | 112 | 114 | 89.7 |
| 5-ALA (30 ppm) | 100 | 126 | 115 | 98.0 |
| 5-ALA (100 ppm) | 100 | 122 | 120 | 103 |
| C. Ex. 3 |  |  |  |  |
| Sun-catch TM (100 ppm) | 100 | 115 | 108 | 102 |

TABLE 21

|  | Respiration activity (CO$_2$ generation %) | | | |
| --- | --- | --- | --- | --- |
|  | Before treatment | After 2 days | After 5 days | After 9 days |
| Ex. 18 |  |  |  |  |
| spreader alone | 100 | 128 | 200 | 123 |
| 5-ALA (30 ppm) | 100 | 96.3 | 139 | 89.2 |
| 5-ALA (100 ppm) | 100 | 114 | 153 | 96.5 |
| C. Ex. 3 |  |  |  |  |
| Sun-catch TM (100 ppm) | 100 | 131 | 184 | 106 |

TABLE 22

|  | Total dry weight (g/pot) |
| --- | --- |
| Ex. 18 |  |
| spreader alone | 2.97 |
| 5-ALA (30 ppm) | 3.83 |
| 5-ALA (100 ppm) | 3.53 |
| C. Ex. 3 |  |
| Sun catch TM (100 ppm) | 3.20 |

As Table 20 clearly shows, the treatment with 5-ALA increased photosynthetic activity. When compared with Comparative Example 3, it was found that this effect of the invention agent was superior to that of Sun-catch TM. As Table 21 clearly shows, the treatment with 5-ALA lowered the respiration activity. When compared with Comparative Example 3, it was found that this effect of the invention agent was superior to that of Sun-catch TM Table 22 shows that the treatment With the invention agent was effective on the total dry plant weight after the treatment. Thus, it was found that the invention agent promoted growth and increased yield. When compared with Comparative Example 3, it was found that these effects of the invention agent were superior to those of Sun-catch TM.

The above Tables 20, 21 and 22 su99est, in total, that the treatment with the invention agent: (1) increased photosynthetic activity; (2) increased plant weight but suppressed the respiration per pot (namely, the effect per biomass exceeded the apparent effect given in Table 21); (3) promoted growth; and (4) elevated yield.

When compared with Comparative Example 3, all of the above-mentioned effects (1) to (4) were superior to those of the marketed plant growth promoter Sun-catch TM.

EXAMPLE 19

Shoot primordia derived from horse radish were aseptically planted into test tubes (40 mm in diameter, 150 mm in height) each containing 30 ml of LS (Linsmaier-Skoog) medium containing 2 ppm of NAA (1-naphthalene acetic acid), 0.02 ppm of BA (benzyladenine), 3% by weight of sucrose and 5-ALA at various concentrations. Then, the shoot primordia were cultured at 25° C. while cyclically irradiating at 6,000 lux for 16 hours and in the dark for 8 hours for 4 weeks. When observed with the naked eye, the plants of the 5-ALA addition groups showed an obvious dark green color, compared with those of the control group. In order to quantitatively analyze the difference in green color, about 4 g of these shoot primordia were ground together with beach sand in an agate mortar and chlorophyll was extracted with acetone/water (ratio by volume 80:15). Then the chlorophyll was redissolved in ethyl ether. After dehydrating, the absorbance was determined at 660 nm and 642.5 nm. Thus, the total chlorophyll content was calculated in accordance with the method described in Shokuhin Kogaku Jikkensho (Yokendo, 1970, p. 496).

Total Chlorophyll Amount (mg/sample (g)) =

$$\frac{Abs. (660 \text{ nm}) \times 7.12 + Abs. (642.5 \text{ nm}) \times 16.5}{\text{Sample Weight (g)}} \times \text{Dilution Ratio}$$

2 tubes were employed for each concentration and the average value was calculated. Table 23 shows the results.

TABLE 23

| 5-ALA conc. (ppm) | Chlorophyll content (mg/100 g) |
| --- | --- |
| 0 | 23.5 |
| 0.01 | 24.7 |
| 0.03 | 25.3 |
| 0.1 | 35.5 |
| 1.0 | 34.0 |
| 3.0 | 35.5 |

TABLE 23-continued

| 5-ALA conc. (ppm) | Chlorophyll content (mg/100 g) |
|---|---|
| 10.0 | 29.1 |

As Table 23 clearly shows, the treatment with 5-ALA increased the chlorophyll content. Thus, it was found that the invention agent contributed to promotion of growth, maintenance of freshness, improvement and maintenance in green color, improvement in photosynthetic activity and improvement in the capability to absorb $CO_2$.

EXAMPLE 20

On Dec. 18, 10 radish seeds (comet, Sakata) were sowed in a 1/5000 a pot filled with field soil to which 10 kg/10 a, in terms of nitrogen, of a compound fertilizer had been applied as the basal dressing. Then, the seeds were cultured in a greenhouse without heating and managed under common conditions. On Feb. 7 (2 to 4 true leaf stage), the seedlings were thinned while leaving 4 seedlings of uniform size per pot. Then, aqueous solutions containing 30 ppm of 5-ALA and 0.1% of various surfactants (for example, anionic surfactants (e.g., TU-21), cationic surfactants (e.g., EX-124, EX-94, EX-122), nonionic surfactants (e.g., Sorbon T-20, Sorbon T-80, TU-54, TU-59, TU-67, EX-118), amphoteric surfactants) were applied to the seedlings by spraying at a dose of 2 ml per pot. After managing in the unheated greenhouse under common conditions, the seedlings were harvested on Mar. 13. Then, the total weight, root part weight and the above-ground part weight of each plant were measured and the average data were calculated. Table 24 shows the results.

TABLE 24

| No. | Weight (g) | | |
|---|---|---|---|
| | Total | Root | Above-ground |
| 1 untreated | 7.8 | 4.4 | 3.4 |
| 2 5-ALA alone | 9.5 | 5.4 | 4.1 |
| 3 + neoesterin | 9.6 | 5.2 | 4.5 |
| 4 + TU-59 | 11.1 | 6.6 | 4.4 |
| 5 + TU-67 | 8.8 | 4.2 | 4.6 |
| 6 + TU-21 | 11.0 | 6.6 | 4.4 |
| 7 + EX-124 | 10.2 | 5.8 | 4.3 |
| 8 + EX-118 | 12.1 | 7.1 | 5.0 |
| 9 + EX-94 | 11.3 | 6.7 | 4.6 |
| 10 + EX-122 | 10.7 | 6.4 | 4.3 |
| 11 + EX-59 | 11.5 | 6.8 | 4.7 |
| 12 + sorbon T-20 | 12.1 | 7.2 | 4.9 |
| 13 + sorbon T-80 | 11.1 | 6.6 | 4.5 |

No. 3: a surfactant produced by Kumiai Chemical Industry Co., Ltd.
No. 4–No. 13: surfactants produced by Toho Chemical Industry Co., Ltd.

Thus, the treatment with 5-ALA clearly promoted growth and increased yield. These effects were exerted on both the above-ground and underground parts of the seedlings. It was further found that these effects were enhanced by adding surfactants and that various surfactants were usable for this purpose.

EXAMPLE 21

On Oct. 5, 5 wheat seeds (Norin No. 61) were sowed in a 1/5000 a pot filled with field soil to which 10 kg/10 a, in terms of nitrogen, of a compound fertilizer had been applied as the basal dressing. Then the seeds were cultured in a greenhouse under common conditions. On Nov. 8, the seedlings were thinned while leaving 4 seedlings of uniform size per pot. Then, these seedlings were cultured under 3,000 lux illumination with a fluorescent lamp from 15 to 22 o'clock. On Jan. 18, aqueous solutions containing 5-ALA at various concentrations and a spreader neoesterin diluted 2,000-fold were sprayed thereon at a dose of 4 ml per pot. After managing under common conditions, water was horizontally hosed upon the plants while were about 50 cm in height on Feb. 4 and thus all of the plants were lodged. Then, the plants were managed as such in a common manner and the recovery ratio was examined on Feb. 8.

4 pots (16 plants) were employed for each concentration. Table 25 shows the results.

TABLE 25

| Conc. (ppm) | No. of recovering plants | Recovery ratio (%) |
|---|---|---|
| 0 | 9 | 56 |
| 30 | 15 | 94 |
| 100 | 16 | 100 |

As Table 25 clearly shows, the treatment with 5-ALA contributed to the growth of good seedlings and thus lodging was reduced. Thus, it was found out that the invention agent was effective in increasing yield.

EXAMPLE 22

On Oct. 5, 5 wheat seeds (Norin No. 61) were sowed in a 1/5000 a pot filled with field soil to which 10 kg/10 a, in terms of nitrogen, of a compound fertilizer had been applied as the base dressing. Then, the seeds were cultured in a greenhouse under common conditions. On Nov. 8, the seedlings were thinned while leaving 4 seedlings of uniform size per pot. Then, these seedlings were cultured under 3,000 lux illumination with a fluorescent lamp from 15 to 22 o'clock. On Feb. 13 (heading/before blooming stage), aqueous solutions containing 5-ALA at various concentrations and a spreader neoesterin diluted 2,000-fold were sprayed thereon at a dose of 4 ml per pot. 10 pots were employed for each concentration. After managing under common conditions, the heads were harvested on Mar. 25 and threshed. Then, the grains were washed with water and less mature ones and impurities were removed. The grains were dried at 80° C. for 24 hours and the weight and grain number per pot were determined. Table 26 shows the results expressed in the average for each concentration.

TABLE 26

| 5-ALA conc. (ppm) | Weight (g/pot) | No. of Grains (No./pot) | Grain weight (mg/grain) |
|---|---|---|---|
| 0 | 6.4 (100%) | 166 (100%) | 38.6 (100%) |
| 30 | 6.7 (105%) | 177 (107%) | 37.9 (98%) |
| 100 | 7.1 (111%) | 180 (108%) | 39.4 (102%) |

As Table 26 clearly shows, the treatment with 5-ALA increased both the weight and grain number, suggesting that yield was thereby increased.

Since no significant difference was observed in grain weight, it was considered that the increase in the matured grains contributed to the increase in yield.

EXAMPLE 23

The procedure of Example 22 was repeated except that 500-fold aqueous solutions of a liquid fertilizer (Hyponex TM; N:P:K=5:10:5 (wt %), produced by Murakami Bussan K. K., Japan (Japanese licensee for Hyponex) containing 5-ALA at various concentrations were applied to the foot of each seedling. Table 27 shows the results.

TABLE 27

| 5-ALA conc. (ppm) | Weight (g/pot) | No. of Grains (No./pot) | Grain weight (mg/grain) |
|---|---|---|---|
| 0 | 7.6 (100%) | 204 (100%) | 37.3 (100%) |
| 30 | 8.5 (112%) | 213 (104%) | 39.9 (107%) |
| 100 | 8.2 (108%) | 206 (101%) | 39.8 (107%) |

As Table 27 clearly shows, the treatment with 5-ALA increased both the weight and grain number, suggesting that the yield was thereby increased.

Since the weight per grain was also increased, it was considered that the treatment with the invention agent contributed to the production of wheat of excellent quality.

EXAMPLE 24

2.5 g portions, on a wet basis, of hairly roots of horse radish derived by a conventional method were planted in a plant jar fermenter (Bioreactor CTB-33, product of Tai-Tech, K. K.) and cultured at 25° C., at a ventilation rate of 0.5 l/min and at 250 rpm using Nitsch media containing various concentrations of 5-ALA. The media were replaced every 7 days. Table 28 shows the weight of hairly roots in the second, third and fourth weeks.

TABLE 28

| 5-ALA conc. (ppm) | Fibrous root weight (g) | | |
|---|---|---|---|
| | 2 week | 3 week | 4 week |
| 0 | 32.2 | 35.2 | 39.6 |
| 0.01 | 34.2 | 39.4 | 44.6 |
| 0.1 | 32.6 | 38.0 | 43.0 |

As Table 28 clearly shows, the treatment with 5-ALA promoted the growth of hairly roots. Thus, it was found that the invention agent was effective in promoting growth and rooting and increasing yield.

EXAMPLE 25

Hairly roots of horse radish were cultured in the same manner as described in Example 24. After 4 weeks, the plants were harvested and the peroxidase (POD) activities thereof were determined. Table 29 shows the results expressed in the POD unit at each 5-ALA concentration.

TABLE 29

| 5-ALA conc. (ppm) | POD activity (U/reactor) |
|---|---|
| 0 | 37,400 |
| 0.01 | 57,400 |
| 0.1 | 55,700 |
| 1 | 56,500 |

As Table 29 clearly shows, the treatment with 5-ALA increased the POD activity per reactor. Thus, it was found that the invention agent was also effective in increasing the yield of a secondary metabolite such as POD.

EXAMPLE 26

On Oct. 12, 15 barley seeds (kashimamugi) were sowed in a 1/2500 a pot filled with field soil to which 10 kg/10 a, in terms of nitrogen, of a compound fertilizer had been applied as the basal dressing. Then, the seeds were cultured as 5-stem training in a greenhouse under long-day illumination. Then, the plants were classified into 2 test lots one of which was treated twice on Dec. 5 (before the blooming stage) and on Dec. 7 (at the blooming stage) while the other one group was treated twice on Dec. 7 (at the blooming stage) and on Dec. 17 (after the blooming stage). Then, they were subjected to foliage treatment with 5-ALA preparations of various concentrations and preparations containing 5-ALA together with epibrassinolide (EBR), each containing a surfactant neoesterin diluted 2,000-fold, at a ratio of 200 l per 10 a.

On Feb. 19, the barley plants were harvested. After drying, the yield of each lot was measured. 18 pots were employed for the untreated lot while 6 pots were employed for each test lot. Tables 30 and 31 show the results expressed as average values.

TABLE 30

| Before blooming stage/blooming stage treatment | | | |
|---|---|---|---|
| | Conc. (ppm) | Yield/pot | Ratio to untreated lot |
| | 5-ALA EBR | (g) | (%) |
| Untreated | 0 0 | 2.10 | 100 |
| 5-ALA | 30 0 | 3.01 | 143 |
| 5-ALA | 100 0 | 2.81 | 134 |
| 5-ALA + EBR | 30 0.01 | 3.19 | 152 |
| 5-ALA + EBR | 100 0.01 | 3.08 | 147 |
| 5-ALA + EBR | 30 0.1 | 3.32 | 158 |
| 5-ALA + EBR | 100 0.1 | 3.29 | 157 |
| EBR | 0 0.01 | 2.34 | 111 |
| EBR | 0 0.1 | 2.57 | 122 |

TABLE 31

| Blooming stage/after blooming stage treatment | | | |
|---|---|---|---|
| | Conc. (ppm) | Yield/pot | Ratio to untreated lot |
| | 5-ALA EBR | (g) | (%) |
| Untreated | 0 0 | 2.10 | 100 |
| 5-ALA | 30 0 | 2.50 | 119 |
| 5-ALA | 100 0 | 2.31 | 110 |
| 5-ALA + EBR | 30 0.01 | 2.60 | 124 |
| 5-ALA + EBR | 100 0.01 | 2.50 | 119 |
| 5-ALA + EBR | 30 0.1 | 2.71 | 129 |
| 5-ALA + EBR | 100 0.1 | 2.90 | 138 |
| EBR | 0 0.01 | 2.11 | 100 |
| EBR | 0 0.1 | 2.20 | 105 |

As Tables 30 and 31 clearly show, treatment with 5-ALA increased the yield. It was further found that the treatment was effective when performed either before, during or after the blooming stage but that the treatment performed before or during the blooming stage was more effective.

It was furthermore found that the combined use of 5-ALA with epibrassinolide enhanced the effects, which indicates that synergistic effects were achieved.

EXAMPLE 27

On Oct. 12, 15 wheat seeds (Norin No. 61) were sowed in a 1/2500 a pot filled with field soil to which 10 kg/10 a, in terms of nitrogen, of a compound fertilizer had been applied as the basal dressing. The seeds were then cultured as 5-stem training in a greenhouse under long-day illumination. Then, the plants were classified into 2 test lots one of which was treated twice on Nov. 29 (before the blooming stage) and on Dec. 5 (at the blooming stage) while the other group was treated twice on Dec. 5 (at the blooming stage) and on Dec. 15 (after the blooming stage). Then, they were subjected to foliage treatment with 5-ALA preparations of various concentrations and preparations containing 5-ALA together with epibrassinolide (EBR), each containing a surfactant neoesterin diluted 2,000-fold, at a ratio of 200 l per 10 a.

On Feb. 28, the wheat plants were harvested. After drying, the yield of each lot was measured. 18 pots were employed for the untreated lot while 6 pots were employed for each test lot. Tables 32 and 33 show the results expressed as average values.

TABLE 32

Before blooming stage/blooming stage treatment

| | Conc. (ppm) | | Yield/pot | Ratio to untreated lot |
|---|---|---|---|---|
| | 5-ALA | EBR | (g) | (%) |
| Untreated | 0 | 0 | 5.60 | 100 |
| 5-ALA | 30 | 0 | 6.60 | 118 |
| 5-ALA | 100 | 0 | 6.31 | 113 |
| 5-ALA + EBR | 30 | 0.01 | 6.63 | 118 |
| 5-ALA + EBR | 100 | 0.01 | 4.40 | 114 |
| 5-ALA + EBR | 30 | 0.1 | 6.68 | 119 |
| 5-ALA + EBR | 100 | 0.1 | 6.55 | 117 |
| EBR | 0 | 0.01 | 6.11 | 109 |
| EBR | 0 | 0.1 | 6.34 | 113 |

TABLE 33

Blooming stage/after blooming stage treatment

| | Conc. (ppm) | | Yield/pot | Ratio to untreated lot |
|---|---|---|---|---|
| | 5-ALA | EBR | (g) | (%) |
| Untreated | 0 | 0 | 5.60 | 100 |
| 5-ALA | 30 | 0 | 6.45 | 115 |
| 5-ALA | 100 | 0 | 6.27 | 112 |
| 5 ALA + EBR | 30 | 0.01 | 6.43 | 115 |
| 5-ALA + EBR | 100 | 0.01 | 6.29 | 112 |
| 5-ALA + EBR | 30 | 0.1 | 6.49 | 116 |
| 5-ALA + EBR | 100 | 0.1 | 6.31 | 113 |
| EBR | 0 | 0.01 | 6.14 | 110 |
| EBR | 0 | 0.1 | 6.21 | 111 |

As Tables 32 and 33 clearly show, the treatment with 5-ALA increased the yield. It was further found that the treatment was effective when performed either before, during or after the blooming stage.

It was furthermore found that the combined use of 5-ALA with epibrassinolide enhanced the effects, which indicates that synergistic effects were achieved.

EXAMPLE 28

Rice seeds (hoshi-no-hikari) were pasteurized with Benlate T (Active ingredient is benomyl by Du Pon't) (diluted 200-fold) over day and night and then incubated in the dark at 30° C., thus hastening germination. After 2 days, 7,000 seeds were sowed in seedling-raising boxes (60 x 30 cm) filled with synthetic cultivation soil. A surfactant (neoesterin) was diluted 2,000-fold with 5-ALA solutions of various concentrations. Then the obtained solutions were sprayed at a ratio of 500 ml per box and then the seeds were covered with soil. After having allowed to stand in the seedling-raising boxes for 2 days, the seedling were grown in a greenhouse.

After 37 days, 50 plants at each concentration were selected at random. The above-ground length and leaf age of each plant were determined. Then the dry above-ground weight of each of 5 plants was measured and the average was calculated. Table 34 shows the results.

TABLE 34

| 5-ALA conc. (ppm) | Above-ground length (cm) (%) | Leaf age | Dry above-ground weight (g/5 plants) (%) |
|---|---|---|---|
| Untreated | 14.9 (100) | 3.28 | 0.115 (100) |
| 0.3 | 15.0 (101) | 3.18 | 0.118 (103) |
| 1 | 15.2 (102) | 3.07 | 0.119 (103) |
| 3 | 14.7 (99) | 3.05 | 0.124 (108) |
| 10 | 15.2 (102) | 3.13 | 0.129 (112) |
| 30 | 15.7 (105) | 3.15 | 0.145 (126) |
| 100 | 15.8 (105) | 3.20 | 0.141 (123) |

As Table 34 clearly shows, the treatment with 5-ALA increased the above-ground weight, while scarcely changing the above-ground leaf age. Thus, it was found that the treatment with the invention agent contributed to the growth of desirable seedlings.

EXAMPLE 29

On Jul. 28, 5 soybean seeds (akishirome) were sowed in a 1/5000 a pot filled with field soil. The seedlings were grown as 4-stem training in a greenhouse. On Aug. 18 (the first compound leaf stage), the seedlings were subjected to foliage treatment with a surfactant (neoesterin) diluted 2,000-fold with 5-ALA solutions of various concentrations at a ratio of 100 l per 10 a. Similarly, soil treatment was performed with the use of the same preparations at a ratio of 100 l per 10 a. On Aug. 30, the growth of the soybean plants was examined and the above-ground weight was measured. Then, the average weight per plant was calculated. Tables 35 and 36 show the results. The fresh weight is the weight immediately after picking and the dry weight is the weight after treating at 80° C. for 24 hours in a drying apparatus.

TABLE 35

| | Foliage treatment | |
|---|---|---|
| 5-ALA conc. | Fresh weight (g;%) | Dry weight (g;%) |
| Untreated | 14.8 (100) | 3.07 (100) |
| 30 ppm | 16.8 (114) | 3.50 (114) |
| 100 ppm | 17.5 (118) | 3.71 (121) |

TABLE 36

| | Soil treatment | |
|---|---|---|
| 5-ALA conc. | Fresh weight (g;%) | Dry weight (g;%) |
| Untreated | 14.8 (100) | 3.07 (100) |
| 30 g/10 a | 16.5 (111) | 3.48 (113) |
| 100 g/10 a | 17.1 (116) | 3.52 (115) |

As Tables 35 and 36 clearly show, the treatment with 5-ALA promoted growth in each case.

EXAMPLE 30

On Oct. 27, 10 soybean seeds (akishirome) were sowed in a 1/5000 a pot filled with field soil. The seedlings were grown as 3-stem training in a greenhouse. On Dec. 21 and 28 (in the early stage of the pod appearing stage following blooming), the plants were subjected to foliage treatment with 200 per 10 a of solutions of 5-ALA at various concentrations each containing a surfactant (neoesterin) diluted 2,000-fold. On Jan. 13, the growth of the soybean plants was examined and pods were weighed. Table 37 shows the results.

TABLE 37

| 5-ALA conc. (ppm) | Total pod weight (g/pot) | Ratio to untreated lot (%) |
| --- | --- | --- |
| Untreated | 14.1 | 100 |
| 10 | 15.4 | 109 |
| 30 | 16.8 | 119 |
| 100 | 15.5 | 110 |
| 300 | 18.5 | 131 |

As Table 37 clearly shows, the treatment with 5-ALA promoted growth and increased yield.

EXAMPLE 31

On Aug. 27, 7 adzuki bean seeds (tamba-dainagon) were sowed in a 1/5000 a pot filled with field soil to which 10 kg/10 a, in terms of nitrogen, of a compound fertilizer had been applied as the basal dressing. The seedlings were grown as 3-stem training in a greenhouse. On Sep. 10 (the first compound leaf stage) and on Sep. 17 (the second compound leaf stage), the plants were subjected to foliage treatment with 100 l per 10 a of solutions of 5-ALA at various concentrations each containing a surfactant (neoesterin) diluted 2,000-fold. On Oct. 1 and on Oct. 11, respectively, the growth of the adzuki bean plants was examined and the above-ground part was weighed. Then the average weight per plant was calculated. Tables 38 and 39 show the results.

TABLE 38

| Treatment in 1st compound leaf stage | | |
| --- | --- | --- |
| 5-ALA conc. (ppm) | Fresh weight (g) (%) | Dry weight (g) (%) |
| Untreated | 4.55 (100) | 1.01 (100) |
| 30 | 4.99 (110) | 1.04 (103) |
| 100 | 5.76 (127) | 1.23 (122) |
| 300 | 4.98 (109) | 1.11 (110) |

TABLE 39

| Treatment in 2nd compound leaf stage | | |
| --- | --- | --- |
| 5-ALA conc. (ppm) | Fresh weight (g) (%) | Dry weight (g) (%) |
| Untreated | 4.41 (100) | 1.13 (100) |
| 30 | 4.71 (107) | 1.19 (105) |
| 100 | 4.90 (111) | 1.21 (107) |
| 300 | 4.71 (107) | 1.18 (104) |

As Tables 38 and 39 clearly show, the treatment with 5-ALA promoted growth. The treatment was effective when performed either in the first compound leaf stage or in the second compound leaf stage, though the former was more effective. The treatment affected the dry weight as well as the fresh weight, which indicates that the invention agent not only increased the moisture content but also promoted the growth of the plants per se.

EXAMPLE 32

On Sep. 10, adzuki bean seeds (tamba-dainagon) were sowed in a 1/5000 a pot filled with field soil to which 10 kg/10 a, in terms of nitrogen, of a compound fertilizer had been applied as the basal dressing. The seedlings were grown as 3-stem training in a greenhouse. On Nov. 22 (in the early part of the pod appearing stage), the plants were subjected to foliage treatment with 500 l per 10 a of solutions of 5-ALA at various concentrations each containing a surfactant (neoesterin) diluted 2,000-fold. On Jan. 18, the growth of the adzuki bean plants was examined and the fresh beans were weighed. Table 40 shows the results.

TABLE 40

| 5-ALA conc. (ppm) | Total bean weight (g/pot) | Ratio to untreated lot (%) |
| --- | --- | --- |
| Untreated | 11.2 | 100 |
| 10 | 11.5 | 103 |
| 30 | 12.2 | 109 |
| 100 | 12.9 | 115 |
| 300 | 17.4 | 155 |

As Table 40 clearly shows, the treatment with 5-ALA promoted growth and increased yield.

EXAMPLE 33

On Dec. 1, corn seeds (pioneer) were sowed on river sand which had been well washed with water. Then they were grown in a greenhouse till the 2.5 leaf stage. On Dec. 14, seedlings of uniform size were selected and the foliage part of each young seedling thus selected was soaked in solutions of 5-ALA at various concentrations each containing a surfactant (neoesterin) diluted 2,000-fold for 5 minutes. When the surface of leaves was dried, the seedlings were transplanted into a 1/5000 a pot filled with field soil to which 10 kg/10 a of a compound fertilizer had been applied as the basal dressing. Then, the seedlings were grown in a greenhouse. On Jan. 12, the growth of the corn plants was examined and the fresh weight was measured. The average per plant was then calculated. Table 41 shows the results.

TABLE 41

| 5-ALA conc. (ppm) | Total weight (g/pot) | Ratio to untreated lot (%) |
| --- | --- | --- |
| Untreated | 7.97 | 100 |
| 3 | 8.51 | 107 |
| 10 | 8.65 | 109 |
| 30 | 9.29 | 117 |
| 100 | 9.38 | 118 |
| 300 | 9.30 | 117 |

As Table 41 clearly shows, the treatment with 5-ALA promoted growth.

In the treatment of this Example, the chemical was never absorbed from roots, different from conventional foliage treatment. Thus, it was found that the invention agent absorbed through leaves exerted the desired effects.

EXAMPLE 34

On Jul. 28, 10 corn seeds (pioneer) were sowed in a 1/2500 a pot filled with field soil to which 10 kg/10 a of a compound fertilizer had been applied as the basal dressing. Then, the seedlings were grown as 4-stem training in a greenhouse. On Aug. 18 (2.5 leaf stage), the plants were subjected to foliage treatment with 100 l per 10 a of solutions of 5-ALA at various concentrations each containing a surfactant (neoesterin) diluted 2,000-fold or to soil treatment therewith similarly at an amount of 100 l per 10 a. On Sep. 3, the growth of the corn plants was examined and the dry above-ground weight was measured. Then the average growth per plant was calculated. Tables 42 and 43 show the results.

TABLE 42

| | Foliage treatment | |
|---|---|---|
| 5-ALA conc. (ppm) | Dry weight (g) | Ratio to untreated lot (%) |
| Untreated | 6.84 | 100 |
| 30 | 8.74 | 127 |
| 100 | 8.08 | 118 |
| 300 | 7.86 | 115 |

TABLE 43

| | Soil treatment | |
|---|---|---|
| 5-ALA conc. (g/10 a) | Dry weight (g) | Ratio to untreated lot (%) |
| Untreated | 6.86 | 100 |
| 30 | 8.50 | 124 |
| 100 | 8.28 | 121 |
| 300 | 8.40 | 122 |

As Tables 42 and 43 clearly show, the treatment with 5-ALA promoted growth, either in the foliage treatment or in the soil treatment.

EXAMPLE 35

On Nov. 15, radish seeds (comet, Sakata) were sowed in a 1/5000 a pot filled with field soil to which 10 kg/10 a, in terms of nitrogen, of a compound fertilizer had been applied as the basal dressing. Then, the seedlings were grown as 3-stem training in a greenhouse. On Dec. 8 (2 leaf stage), 15, 21 and 28, the seedlings were subjected to foliage treatment each with a solution of 100 ppm of 5-ALA containing a surfactant (neoesterin) diluted 2,000-fold at a ratio of 200 l/10 a. On Jan. 12, the growth of the radish plants was examined and the fresh weight was measured. The average growth per plant was calculated. Table 44 shows the results.

TABLE 44

| Date | Fresh weight (g) | Ratio to untreated lot (%) |
|---|---|---|
| Untreated | 18.0 | 100 |
| 12/8 | 20.5 | 114 |
| 12/15 | 21.8 | 121 |
| 12/21 | 22.2 | 123 |
| 12/28 | 21.4 | 119 |

As Table 44 clearly shows, the treatment with 5-ALA promoted growth and increased yield. The invention agent exerted its effects when applied in any stage, which suggested that it was applicable over a wide range of period.

EXAMPLE 36

10 kg/10 a, in terms of nitrogen, of a compound fertilizer was applied to a field as the basal dressing and 2 ridges (80 cm in width, 5 m in length) were formed. On Sep. 12, 10 1/10 a of radish seeds (comet) were sowed therein and grown under common conditions. A surfactant (neoesterin) was diluted 2,000-fold with 5-ALA solutions of various concentrations. Then, the seedlings were subjected to foliage treatment with 200 per 10 a of the solutions on Sep. 26 (2.5 leaf stage) in the case of the 1-treatment lot and on Sep. 26 and on Oct. 16 in the case of the 2-treatment lot. On Oct. 29, the radishes were harvested and their fresh weight was measured. The average weight per plant was calculated. Tables 45 and 46 show the results.

TABLE 45

| | 1-Treatment lot | |
|---|---|---|
| 5-ALA conc. (ppm) | Fresh weight (g) | Ratio to untreated lot (%) |
| Untreated | 30.5 | 100 |
| 30 | 36.7 | 120 |
| 100 | 44.3 | 145 |
| 300 | 40.2 | 132 |

TABLE 46

| | 2-Treatment lot | |
|---|---|---|
| 5-ALA conc. (ppm) | Fresh weight (g) | Ratio to untreated lot (%) |
| Untreated | 30.5 | 100 |
| 30 | 40.2 | 132 |
| 100 | 44.6 | 147 |
| 300 | 48.4 | 159 |

As Tables 45 and 46 clearly show, the treatment with 5-ALA promoted growth and increased yield in field cultivation.

It was further found that the effects were enhanced by performing the treatment twice, which suggested that repeated treatment was effective.

EXAMPLE 37

10 kg/10 a, in terms of nitrogen, of a compound fertilizer was applied as the basal dressing to a field the pH of which had been adjusted to 6.8 with slaked lime. Then two ridges (110 cm in width, 5 m in length) were formed. On Nov. 6, 15 1/10 a of spinach seeds (Autumn horenso) were sowed in each ridge in 3 lines. On Nov. 15, the ridges were coated with a vinyl sheet and then plastic greenhouse (tunnel) cultivation was performed in a conventional manner. On Dec. 12, the plants were subjected to foliage treatment with 200 l per 10 a of 5-ALA solutions of various concentrations each containing a surfactant (neoesterin) diluted 2,000-fold. At the application, the spinach seedlings were in the 3 to 5 true leaf stage. On Jan. 17, the plants were harvested and their fresh weight was determined. Table 47 shows the results expressed as the average fresh weight per plant.

TABLE 47

| 5-ALA conc. (ppm) | Fresh weight (g) | Ratio to untreated lot (%) |
|---|---|---|
| Untreated | 9.77 | 100 |
| 10 | 12.1 | 124 |
| 30 | 11.7 | 120 |
| 100 | 12.3 | 126 |
| 300 | 10.9 | 112 |

As Tables 47 clearly shows, the treatment with 5-ALA also promoted growth and increased yield in field cultivation.

EXAMPLE 38

Pollens of tea plant flowers were inoculated into agar media (agar 1%) containing 10% sucrose and 5-ALA at various concentrations and incubated therein at 28° C. in the dark. After 24 hours, the elongation of the pollen tubes was measured. Table 48 shows the results.

TABLE 48

| 5-ALA conc. (ppm) | Average elongation (mm) | Ratio to untreated lot (%) |
|---|---|---|
| Untreated | 3.0 | 100 |

TABLE 48-continued

| 5-ALA conc. (ppm) | Average elongation (mm) | Ratio to untreated lot (%) |
|---|---|---|
| 0.001 | 3.6 | 120 |
| 0.01 | 4.1 | 137 |

As Table 48 clearly shows, 5-ALA promoted growth of the organ.

EXAMPLE 39

Korean lawn grass planted 10 years ago was divided into sections (50 cm×50 cm) and runners located boundary lines were cut with a cutter. Then, the grass was subjected to foliage treatment with 200 l per 10 a of 5-ALA solutions of various concentrations each containing a surfactant (neoesterin) diluted 2,000-fold. 1-Treatment lots were treated on Oct. 4, while 2-treatment lots were treated on Oct. 4 and 27. On Dec. 7, 17 and 25 and on Jan. 9, the green color of the grass was evaluated. Table 49 shows the results.

TABLE 49

| Date | 1-Treatment lot | | | | 2-Treatment lot | | | |
|---|---|---|---|---|---|---|---|---|
| 5-ALA conc. | 12/7 | 12/17 | 12/25 | 1/9 | 12/7 | 12/17 | 12/25 | 1/9 |
| Untreated | 3.0 | 3.0 | 3.0 | 3.0 | 3.0 | 3.0 | 3.0 | 3.0 |
| 10 ppm | 3.5 | 4.0 | 3.0 | 3.0 | 3.5 | 2.0 | 3.0 | 3.0 |
| 30 ppm | 3.5 | 3.5 | 3.0 | 3.0 | 4.0 | 4.0 | 3.0 | 3.0 |
| 100 ppm | 4.0 | 4.0 | 3.5 | 3.0 | 4.0 | 5.0 | 4.0 | 3.0 |
| 300 ppm | 3.0 | 3.5 | 3.5 | 3.0 | 3.0 | 4.0 | 3.0 | 3.0 |
| 1000 ppm | 2.5 | 2.5 | 2.5 | 3.0 | 2.0 | 2.5 | 2.5 | 3.0 |

The evaluation data were expressed in relative values of from 1.0 to 5.0, where the value of the untreated lot was 3.0. A higher value means a deeper green color. As Table 49 clearly shows, the treatment with the invention agent contributed to the maintenance of green color for a prolonged period of time.

EXAMPLE 40

Korean lawn grass planted 10 years ago was divided into sections (50 cm×50 cm) and runners located boundary lines were cut with a cutter. Then, the grass was subjected to foliage treatment with 200 l per 10 a of 5-ALA solutions of various concentrations each containing a surfactant (neoesterin) diluted 2,000-fold. 1-Treatment lots were treated on Oct. 4, while 2-treatment lots were treated on Oct. 4 and 27. On Jan. 23, the growth of the Korean lawn grass was examined. 4 samples (10.4 cm in diameter, 10 cm in depth) were collected from each section. After washing with water and drying, the dry weight was measured. Table 50 shows the results.

TABLE 50

| 5-ALA conc. (ppm) | 1-Treatment | | 2-Treatment | |
|---|---|---|---|---|
| | Dry weight (g) | Ratio to untreated lot (%) | Dry weight (g) | Ratio to untreated lot (%) |
| 0 | 22.3 | 100 | 24.7 | 100 |
| 10 | 26.0 | 117 | 27.3 | 111 |
| 30 | 25.3 | 113 | 25.7 | 104 |
| 100 | 24.1 | 108 | 25.7 | 104 |
| 300 | 23.6 | 106 | 25.7 | 104 |

As Table 50 clearly shows, the treatment with 5-ALA promoted the growth of the lawn grass.

EXAMPLE 41

2 ridges (2 m in width, 8 m in length), to which 10 kg/10 a, in terms of nitrogen, of a compound fertilizer had been applied as the basal dressing, were formed and 5 kg per 10 a of wheat seeds (norin No. 50) were sowed on Oct. 24. After growing under common conditions, the plants were subjected to foliage treatment with 200 l per 10 a of 5-ALA solutions of various concentrations or 5-ALA and epibrassinolide mixtures, each containing a surfactant (neoesterin) diluted 2,000-fold, twice on May 10 (before blooming stage) and on May 17 (blooming stage). 3 treated lots were employed. On Jul. 19, the harvested wheat was weighed. Table 51 shows the results.

TABLE 51

| | Conc. (ppm) | | Yield (kg/10 a) | Ratio to untreated lot (%) |
|---|---|---|---|---|
| | 5-ALA | EBR | | |
| Untreated | 0 | 0 | 48.3 | 100 |
| 5-ALA | 30 | 0 | 52.1 | 108 |
| 5-ALA | 100 | 0 | 52.5 | 109 |
| 5-ALA + EBR | 30 | 0.1 | 52.9 | 110 |
| 5-ALA + EBR | 100 | 0.1 | 52.6 | 109 |

As Table 51 clearly shows, the treatment with 5-ALA increased yield. The combined use of 5-ALA with EBR further showed synergistic effects.

EXAMPLE 42

2 ridges (2 m in width, 8 m in length), to which 10 kg/10 a, in terms of nitrogen, of a compound fertilizer had been applied as the basal dressing, were formed and 5 kg per 10 a of barley seeds (haruna nijo) were sowed on Oct. 20. After growing under common conditions, the plants were subjected to foliage treatment with 200 per 10 a of 5-ALA solutions of various concentrations or 5-ALA and epibrassinolide mixtures, each containing a surfactant (neoesterin) diluted 2,000-fold, twice on May 7 (before blooming stage) and on May 14 (blooming stage). 3 treated lots were employed. On Jul. 23, the harvested barley was weighed. Table 52 shows the results.

TABLE 52

| | Conc. (ppm) | | Yield (kg/10 a) | Ratio to untreated lot (%) |
|---|---|---|---|---|
| | 5-ALA | EBR | | |
| Untreated | 0 | 0 | 45.1 | 100 |
| 5-ALA | 30 | 0 | 57.7 | 128 |
| 5-ALA | 100 | 0 | 52.8 | 117 |
| 5-ALA + EBR | 30 | 0.1 | 57.9 | 128 |
| 5-ALA + EBR | 100 | 0.1 | 57.5 | 127 |

As Table 52 clearly shows, the treatment with 5-ALA increased yield. The combined use of 5-ALA with EBR further showed synergistic effects.

EXAMPLE 43

On Oct. 12, 15 wheat seeds (norin No. 61) were sowed in a 1/2500 a pot filled with field soil, to which 10 kg/10 a, in terms of nitrogen, of a compound fertilizer had been applied as the base dressing, and grown as 5-stem training in a greenhouse under long-day illumination. On Nov. 2 (before the blooming stage) and on Dec. 5 (blooming stage), the plants were subjected to foliage treatment with 8 ml per pot (200 1/10 a) of 5-ALA solutions of various concentrations each containing a spreader (neoesterin) diluted 2,000-fold using a sprayer. 6 pots were employed for each treatment. Following Feb. 12, one pot was harvested every other day and the ratio of matured grains was examined. Table 53 shows the results.

TABLE 53

| 5-ALA conc. (ppm) | Matured grains (%) | | | | | |
|---|---|---|---|---|---|---|
|  | 2/12 | 2/14 | 2/16 | 2/18 | 2/20 | 2/22 |
| 0 | 6 | 11 | 43 | 70 | 92 | 98 |
| 30 | 8 | 15 | 52 | 88 | 96 | 100 |
| 100 | 7 | 18 | 61 | 85 | 98 | 100 |

As Table 53 clearly shows, the treatment with 5-ALA shortened the time required for maturing.

EXAMPLE 44

Korean lawn grass planted 10 years ago was transplanted into a 1/2500 a pot filled with field soil, to which 10 kg/10 a, in terms of nitrogen, of a compound fertilizer had been applied as the basal dressing. After managing under common conditions, 6 pots showing uniform growth were selected on Jul. 31. Then, the carbon dioxide gas absorption and respiration were determined by the same method as employed in Example 18 except that illumination was performed at 80,000 lux. Then, a 1,000-fold dilution of neoesterin and the same solution containing 100 ppm of 5-ALA were sprayed respectively onto 3 pots at a ratio of 300 l per 10 a.

The plants were then managed under common conditions. On Aug. 1 (the next day after the application), 3 (3 days thereafter), 7 (7 days thereafter) and 14 (14 days thereafter), the $CO_2$ absorption concentration and the increase in $CO_2$ due to respiration were determined by the same method as performed on Jul. 31. The increase in $CO_2$ at each point for each pot was calculated with the data on Jul. 31 being taken as 100%. Then, the average of the data of 3 pots for each condition was determined. Tables 54 and 55 show the results.

TABLE 54

| Photosynthetic activity ($CO_2$ absorption %) | | | | | |
|---|---|---|---|---|---|
|  | Before treatment | After 1 day | After 3 days | After 7 days | After 14 days |
| Spreader alone | 100 | 101 | 111 | 123 | 127 |
| 5-ALA 100 ppm | 100 | 117 | 146 | 149 | 146 |

TABLE 55

| Respiration activity ($CO_2$ generation %) | | | | | |
|---|---|---|---|---|---|
|  | Before treatment | After 1 day | After 3 days | After 7 days | After 14 days |
| Spreader alone | 100 | 114 | 140 | 143 | 155 |
| 5-ALA 100 ppm | 100 | 101 | 113 | 111 | 128 |

As Tables 54 and 55 clearly show, the treatment with 5-ALA enhanced photosynthetic activity and simultaneously suppressed respiration activity.

EXAMPLE 45

To lawn grass pots, which were prepared and treated in the same manner as described in Example 44, 200 g per 10 a of Shimazine TM (a triazine-series herbicide; AI is CAT by Ciba-Geigy AG.) was applied. Next, a 1,000-fold dilution of neoesterin and the same solution containing 100 ppm of 5-ALA were sprayed respectively onto 3 pots at a ratio of 300 l per 10 a.

The plants were then managed under common conditions. On Aug. 1 (the next day after the application), 3 (3 days thereafter), 7 (7 days thereafter) and 14 (14 days thereafter), the $CO_2$ absorption concentration was determined by the same method as performed on Jul. 31. The $CO_2$ concentration at each point for each pot was calculated with the data on Jul. 31 being taken as 100%. Then, the average of the data of 3 pots for each condition was determined. Table 56 shows the results.

TABLE 56

| Photosynthesis activity ($CO_2$ absorption %) | | | | | |
|---|---|---|---|---|---|
|  | Before treatment | After 1 day | After 3 days | After 7 days | After 14 days |
| Spreader alone | 100 | 101 | 79 | 79 | 106 |
| 5-ALA 100 ppm | 100 | 114 | 91 | 102 | 137 |

When the data given in the above Table 56 were compared with those of Table 54 in Example 44, it was found that the photosynthetic activity was lowered by the chemical damage due to the herbicide Shimazine.

As Table 56 clearly shows, the chemical damage due to Shimazine on photosynthetic activity was significantly relieved by the addition of 5-ALA and plant recovery was thereby promoted.

EXAMPLE 46

10 kg/10 a, in terms of nitrogen, of a compound fertilizer was applied to a field as the basal dressing and a ridge 1 m in width was formed. On Apr. 12, 10 l per 10 a of komatsuna seeds (maruba komatsuna, Nohara Shubyo K. K.) were sowed and then managed under common conditions. On Apr. 25, the seedlings were thinned. Thus, 9 test sections (1 m × 1 m) were prepared at intervals of 50 cm.

On May 13, the seedlings were subjected to foliage treatment with 5-ALA aqueous solutions of 0, 30 and 100 ppm each containing a surfactant (neoesterin) diluted 1,000-fold. 100 ml portions of the solution of each concentration was applied to 3 sections.

On May 23, the above-ground parts of the plants were harvested and the fresh weight was determined. The average weight per plant was then calculated. Table 57 shows the results.

TABLE 57

| 5-ALA conc. (ppm) | Fresh weight (g/plant) | Ratio to untreated lot (%) |
|---|---|---|
| 0 | 11.6 | 100 |
| 30 | 13.2 | 114 |
| 100 | 12.8 | 110 |

As Table 57 clearly shows, treatment with 5-ALA increased yield.

EXAMPLE 47

The procedure of Example 46 was repeated except that the komatsuna seeds were replaced by rape seeds (norin No. 20, Nohara Shubyo K. K.). Table 58 shows the results.

TABLE 58

| 5-ALA conc. (ppm) | Fresh weight (g/plant) | Ratio to untreated lot (%) |
|---|---|---|
| 0 | 10.2 | 100 |
| 30 | 11.2 | 110 |
| 100 | 14.3 | 140 |

As Table 58 clearly shows, treatment with 5-ALA increased yield.

EXAMPLE 48

10 kg/10 a, in terms of nitrogen, of a compound fertilizer was applied to a field as the basal dressing and a ridge 1 m in width and 10 m in length was formed. On Mar. 26, potato seed tubers (danshaku, Nohara Shubyo) were planted in 2 lines at intervals of about 50 cm. Then, the plants were managed under common conditions and buds were picked in such a manner as to leave 2 buds per plant. On Jul. 2, the seedlings were subjected to foliage treatment with 200 1/10 a of 5-ALA aqueous solutions of 0 and 100 ppm each containing a surfactant (neoesterin) diluted 1,000-fold. On Jul. 23, the potatoes were harvested and the number and weight were determined. Table 59 shows the results.

TABLE 59

| 5-ALA conc. (ppm) | 0 | 100 |
|---|---|---|
| No. of plants | 44 | 40 |
| Yield (g/plant) | 344 | 560 |
| Ratio to untreated lot (%) | 100 | 163 |
| No. of potatoes | 4.8 | 6.9 |
| Ratio to untreated lot (%) | 100 | 144 |
| Average weight (g/potato) | 71.1 | 81.1 |
| Ratio to untreated lot (%) | 100 | 114 |

As Table 59 clearly shows, treatment with 5-ALA greatly increased yield. In particular, the yield per plant was increased by 63% and the weight per potato was also greatly increased, suggesting marked effects.

EXAMPLE 49

10 kg/10 a, in terms of nitrogen, of a compound fertilizer was applied to a field as the basal dressing and 3 ridges 1 m in width and 4 m in length were formed. On Oct. 5, garlic bulbs (Fukuchi White) were planted and managed under common conditions. On May 13, the plants were subjected to foliage treatment with 200 1/10 a of 5-ALA aqueous solutions of 0, 30 and 100 ppm each containing a surfactant (neoesterin) diluted 1,000-fold. On Jun. 5, the plants were harvested and the edible parts weighed. Table 60 shows the results.

TABLE 60

| 5-ALA conc. (ppm) | Yield (g/plant) | Ratio to untreated lot (%) |
|---|---|---|
| 0 | 29.4 | 100 |
| 30 | 41.3 | 140 |
| 100 | 41.4 | 141 |

As Table 60 clearly shows, treatment with 5-ALA increased yield.

EXAMPLE 50

On May 15, soybean seeds (gokuwaseshiroge grand prix; Takayama Shubyo K. K.) were sowed in a 1/2500 a pot filled with field soil to which 15 kg/10 a, in terms of nitrogen, of a compound fertilizer had been applied as the basal dressing. The seedlings were grown as 3-stem training per pot and managed under common conditions.

Then, the plants were subjected to foliage treatment with 5-ALA solutions of 30 and 100 ppm, each containing a surfactant (neoesterin) diluted 2,000-fold. The time and dose of the treatment were as listed in Tables 61 and 62. 3 treated lots and 6 untreated lots were prepared.

On Jul. 28, the plants were harvested and the yield was examined. Tables 61 and 62 show the results.

TABLE 61

| Treatment with 30 ppm of 5-ALA Data given in parentheses are based on the untreated lot (%). | | | | | |
|---|---|---|---|---|---|
| Date | Stage | Dose (l/10 a) | Pod weight (g/pod) | Bean weight (g/bean) | Yield (g/plant) |
| Untreated | — | — | 1.76 (100) | 0.52 (100) | 15.9 (100) |
| 5/15 | True leaf 1 | 200 | 2.04 (116) | 0.60 (116) | 16.7 (105) |
| 5/31 | Compound leaf 1 | 200 | 1.99 (113) | 0.55 (105) | 16.1 (102) |
| 6/5 | Compound leaf 2 | 200 | 1.87 (106) | 0.54 (105) | 17.6 (111) |
| 6/14 | Compound leaf 3 | 200 | 1.93 (110) | 0.58 (111) | 16.0 (101) |
| 6/26 | Compound leaf 5 (blooming) | 200 | 1.79 (102) | 0.57 (111) | 15.1 (95) |
| 7/3 | Early pod appearing | 300 | 2.00 (114) | 0.62 (119) | 17.5 (110) |
| 7/11 | Medium pod appearing | 300 | 1.76 (100) | 0.55 (105) | 15.9 (100) |

TABLE 62

| Treatment with 100 ppm of 5-ALA Data given in parentheses are based on the untreated lot (%). | | | | | |
|---|---|---|---|---|---|
| Date | Stage | Dose (l/10 a) | Pod weight (g/pod) | Bean weight (g/bean) | Yield (g/plant) |
| Untreated | — | — | 1.76 (100) | 0.52 (100) | 15.9 (100) |
| 5/15 | True leaf 1 | 200 | 2.08 (118) | 0.61 (117) | 16.8 (106) |
| 5/31 | Compound leaf 1 | 200 | 2.17 (124) | 0.62 (120) | 18.9 (119) |
| 6/5 | Compound leaf 2 | 200 | 2.08 (118) | 0.57 (110) | 17.1 (108) |
| 6/14 | Compound leaf 3 | 200 | 1.89 (107) | 0.59 (114) | 17.9 (113) |
| 6/26 | Compound leaf 5 (blooming) | 200 | 2.01 (114) | 0.64 (123) | 15.5 (98) |
| 7/3 | Early pod appearing | 300 | 1.95 (111) | 0.61 (118) | 16.2 (102) |

TABLE 62-continued

Treatment with 100 ppm of 5-ALA
Data given in parentheses are based on the untreated lot (%).

| Date | Stage | Dose (l/10 a) | Pod weight (g/pod) | Bean weight (g/bean) | Yield (g/plant) |
|---|---|---|---|---|---|
| 7/11 | Medium pod appearing | 300 | 2.07 (118) | 0.61 (118) | 16.4 (104) |

As Tables 61 and 62 show, treatment with 5-ALA increased yield. In particular, the treatment was effective when performed in the seedling stage (true leaf stage 1 to compound leaf stage 2) and the bean maturing stage (pod appearing stage). In the blooming stage, both the pod weight and bean weight were increased, though the yield was rather decreased. The bean weight, which most largely affected quality, reached a maximum level in this stage. These facts indicated that treatment with 5-ALA suppressed seed setting and thus beans of high quality were obtained. Thus, it was found that the treatment with the invention agent contributed not only to an increase in yield but also to an adjustment of seed setting and to an improvement in the quality, when performed at an appropriate stage.

EXAMPLE 51

10 kg/10 a, in terms of nitrogen, of a compound fertilizer was applied to a field as the basal dressing and 4 ridges 1 m in width were formed. On Oct. 24, 5 kg/10 a of wheat seeds (norin No. 61) were sowed in 2 lines at intervals of 50 cm.

On May 5 and 10, the seedlings were subjected to foliage treatment with 200 l per 10 a of 5-ALA aqueous solutions of various concentrations each containing a surfactant (neoesterin) diluted 2,000-fold. A section (1 m × 1 m) was employed for each condition and 4 lots were employed as treated ones. 8 lots were employed as untreated ones.

On Jul. 12, the plants were harvested and the total grain weight was determined by the random sampling method (20 heads per lot).

Table 63 shows the results.

TABLE 63

| 5-ALA conc. (ppm) | Yield (g/20 heads) | Ratio to untreated lot (%) |
|---|---|---|
| 0 | 31.7 | 100 |
| 10 | 32.9 | 104 |
| 30 | 34.1 | 107 |
| 100 | 36.0 | 114 |

As Table 63 clearly shows, treatment with 5-ALA also increased yield in the field test.

EXAMPLE 52

On Apr. 6, spring wheat seeds (haruyutaka) were sowed in a 1/2500 a pot filled with soil to which 10 kg/10 a, in terms of nitrogen, of a compound fertilizer was applied as the basal dressing. Then the plants were grown as 3-stem training in a glass greenhouse under common conditions.

On May 21 and 28, the plants were subjected to foliage treatment with 200 l per 10 a of 5-ALA aqueous solutions of 10, 30 and 100 ppm each containing a surfactant (neoesterin) diluted 2,000-fold. 6 treated lots were employed and 14 lots were employed as untreated ones.

On Jul. 13, the plants were harvested and the total head weight and threshed grain weight (per head) were determined. Table 64 shows the results.

TABLE 64

| 5-ALA conc. (ppm) | Head weight (g/head) | Ratio to untreated lot (%) | Grain weight (g/head) | Ratio to untreated lot (%) |
|---|---|---|---|---|
| 0 | 1.53 | 100 | 1.17 | 100 |
| 10 | 1.75 | 114 | 1.35 | 115 |
| 30 | 1.62 | 106 | 1.26 | 108 |
| 100 | 1.65 | 108 | 1.28 | 109 |

Table 64 shows that treatment With 5-ALA also increased the yield of spring wheat.

EXAMPLE 53

On May 9, kidney bean seeds (Cyprus, Takii & Co., Ltd.) were sowed in a 1/2500 a pot filled with soil to which 15 kg/10 a, in terms of nitrogen, of a compound fertilizer was applied as the basal dressing. Then the plants were grown as 3-stem training in a glass greenhouse under common conditions. The plants were then subjected to foliage treatment with 200 l per 10 a of a 5-ALA aqueous solution of 100 ppm containing a surfactant (neoesterin) diluted 2,000-fold at the points listed in Table 65. 3 treated lots were employed and 6 lots were employed as untreated ones.

On Jul. 3, the plants were harvested and the yield was determined. Table 65 shows the results.

TABLE 65

Data given in parentheses are based on the untreated lot (%).

| Date | Stage | Pod weight (g/pod) | Yield (g/plant) |
|---|---|---|---|
| Untreated | — | 1.30 (100) | 10.55 (100) |
| 5/20 | True leaf 1 | 1.50 (116) | 12.57 (119) |
| 5/25 | Compound leaf 1 | 1.43 (110) | 13.68 (130) |
| 5/31 | Compound leaf 2 | 1.32 (102) | 10.71 (102) |
| 6/5 | Compound leaf 3 | 1.06 (82) | 9.29 (88) |
| 6/13 | Compound leaf 5 (blooming) | 1.13 (87) | 9.06 (86) |
| 6/18 | Early pod appearing | 1.24 (95) | 11.34 (108) |
| 6/26 | Pod maturing | 1.31 (101) | 11.28 (107) |

As Table 65 shows, treatment with the invention agent increased yield. It was found that this treatment was particularly effective when performed in the seedling stage (true leaf period 1 to compound leaf period 2).

EXAMPLE 54

20 kg/10 a, in terms of nitrogen, of a compound fertilizer was applied to a field as the basal dressing and a ridge 2 m in width was formed. On Nov. 1, garlic bulbs (Fukuchi White, Nohara Shubyo, K.K.) were planted in 8 lines at intervals of 25 cm. Then, the plants were managed under common conditions. On Apr. 20 (5.5 leaf stage), when underground bulbs began to mature, the seedlings were subjected to foliage treatment with 200 l/10 a of 5-ALA aqueous solutions of 0, 30, 100 and 300 ppm and a comparative agent (aqueous solution of a garlic yield-increasing agent Sun-catch, product of Mitsubishi Gas Chemical Co., Ltd.), each containing a surfactant (neoesterin) diluted 1,000-fold.

Each test section (50+50 cm) had 4 plants and the treatment was repeated 6 times for each condition.

The plants were harvested on Jun. 6 and the yield was measured. Tables 66 and 67 show the results.

TABLE 66

| 5-ALA conc. (ppm) | Data given in parentheses are based on the untreated lot (%). | |
|---|---|---|
| | Underground weight (g/bulb) | Bulb size (cm) |
| Untreated | 22.2 (100) | 3.94 (100) |
| 30 | 27.3 (123) | 4.18 (106) |
| 100 | 26.2 (118) | 4.19 (106) |
| 300 | 28.6 (129) | 4.26 (108) |
| Sun-Catch TM (choline chloride; 1,000) | 26.0 (117) | 4.17 (106) |

As Table 66 clearly shows, the treatment with the invention agent remarkably increased yield. This effect exceeded the one achieved by the comparative agent Sun-catch TM. Further, the bulb size was increased by treatment with the invention agent, indicating that the qualities of the garlic were improved.

TABLE 67

| 5-ALA conc. (ppm) | Ratio of weight/bulb (%) | | |
|---|---|---|---|
| | ≧30 g | 30 g > and ≧ 20 g | <20 g |
| Untreated | 18 | 39 | 43 |
| 30 | 36 | 28 | 36 |
| 100 | 37 | 35 | 28 |
| 300 | 37 | 38 | 25 |
| Sun-catch TM (choline chloride; 1,000) | 27 | 40 | 33 |

As Table 67 clearly shows, treatment with the invention agent increased the ratio of large bulbs of higher commercial value and decreased the ratio of small bulbs of lower commercial value. That is to say, it was found out that the quality of the garlic was improved by treatment with the invention agent.

EXAMPLE 55

On Feb. 5, radish seeds (comet, Sakata Shubyo K. K.) were sowed in a 1/5000 a pot filled with field soil to which 10 kg/10 a, in terms of nitrogen, of a compound fertilizer had been applied as the basal dressing. The seedlings were grown as 3-stem training per pot in a glass greenhouse under common conditions. On Mar. 20, (5.5 leaf stage), the plants were subjected to foliage treatment with 200 l/10 a of 5-ALA aqueous solutions of 0 and 100 ppm each containing a surfactant (neoesterin) diluted 2,000-fold. 10 pots were employed for each concentration. Then, the quantity of light was reduced to 40% by covering the plants with cheese cloth and the cultivation was continued in a common manner.

On Apr. 5, the plants were harvested and weighed. Table 68 shows the results.

TABLE 68

| 5-ALA conc. (ppm) | Total weight (g/plant) | Underground total weight (g/plant) | Ratio of weight of 35 g or more to total weight (%) |
|---|---|---|---|
| 0 | 26.0 (100) | 12.4 (100) | 15.0 |
| 100 | 32.4 (125) | 15.7 (126) | 48.2 |

As Table 68 clearly shows, treatment with 5-ALA increased yield and improved quality even under reduced light conditions.

In the test lot, good plants weighing 35 g or more amounted to almost a half of the total plants, while the ratio thereof in the control lot was as low as 15%. Thus, it was found out that the environmental stress (i.e., light reduction) was relieved by treatment with 5-ALA.

EXAMPLE 56

On May 20, rice seedlings (hoshi-no-hikari; 3 leaf stage) were planted in a 1/2000 a pot filled with paddy field soil to which 30 kg/10 a, in terms of nitrogen, of a compound fertilizer had been applied as the basal dressing. 4 seedlings were planted per pot at a depth of 3 cm. These plants were grown outdoor under common conditions at a water depth of 3 cm. On Jun. 20, the seedlings were thinned so as to give 3 stems per pot. On Jul. 23, 15 kg/10 a, in terms of nitrogen, of a compound fertilizer was applied as the top dressing.

On Jul. 26 (head formation stage) and on Aug. 22 (blooming stage following head appearing stage), the seedlings were subjected to watering treatment with 5-ALA at the concentrations as listed in Table 69. On Oct. 5, the rice plants were harvested. After drying, the head weight per plant was measured. 3 pots were employed for each condition and the average value of 9 plants was calculated. Table 69 shows the results.

TABLE 69

| No. of treatments (date) | Head weight (dry weight/plant) Data given in parentheses are based on the untreated lot (%). | | | | | |
|---|---|---|---|---|---|---|
| | 5-ALA conc. (g/10 a) | | | | | |
| | 0 | 3 | 10 | 30 | 100 | 300 |
| 1 (7/26) | 22.0 (100) | 24.2 (110) | 25.1 (114) | 24.5 (111) | 25.2 (115) | 23.6 (107) |
| 1 (8/22) | 22.0 (100) | 23.8 (108) | 24.2 (110) | 24.0 (109) | 25.1 (114) | 24.4 (111) |
| 2 (7/26, 8/22) | 22.0 (100) | 23.8 (108) | 24.0 (109) | 25.4 (115) | 26.0 (118) | 24.3 (110) |

As Table 69 clearly shows, treatment with 5-ALA increased yield. Thus, it was found that the invention agent was also effective when used in watering, namely, when used in soil treatments.

EXAMPLE 57

A field, to which 3 kg/10 a, in terms of nitrogen, of a compound fertilizer had been applied as the basal dressing, was divided into 20 sections (1 m×1 m). Sweet potato seedlings (beniazuma) were soaked in 5-ALA aqueous solutions of concentrations as given in Table 70 and in an aqueous solution of Sun-catch TM for 24 hours. After soaking, the seedlings were planted on Jun. 26 at a ratio of 4 seedlings per section. 3 sections were employed for each condition while 5 sections were employed for untreated seedlings. The seedlings were then managed under common conditions.

On Oct. 18, the plants were harvested and the potato yield per section and the average weight per potato were examined. Table 70 shows the results.

TABLE 70

| Data given in parentheses are based on the untreated lots (%). | | | | | | |
|---|---|---|---|---|---|---|
| | 5-ALA conc. (ppm) | | | | | Sun-catch TM (choline chloride; ppm) |
| | 0 | 0.001 | 0.01 | 0.1 | 1 | 20 |

TABLE 70-continued

| Yield (g/section) | 1552 (100) | 1677 (106) | 1972 (127) | 1875 (121) | 1634 (105) | 1743 (112) |
|---|---|---|---|---|---|---|
| Average wt. (g/potato) | 120 (100) | 128 (107) | 171 (143) | 136 (114) | 114 (95) | 148 (124) |

As Table 70 clearly shows, treatment with the invention agent increased yield and improved quality.

EXAMPLE 58

A field, to which 3 kg/10 a, in terms of nitrogen, of a compound fertilizer had been applied as the basal dressing, was divided into 20 sections (1 m × 1 m). On Jun. 25, sweet potato seedlings (beniazuma) were planted at a ratio of 4 seedlings per section. 3 sections were employed for each condition while 5 sections were employed for untreated seedlings. The seedlings were then managed under common conditions. On Jul. 18 (23 days after the plantation), the seedlings were subjected to foliage treatment with 100 l per 10 a of 5-ALA solutions of concentrations as given in Table and Sun-catch TM aqueous solution, each containing a surfactant (neoesterin) diluted 2,000-fold.

On Oct. 18, the plants were harvested and the potato yield per section and the average weight per potato were examined. Table 71 shows the results.

TABLE 71

Data given in parentheses are based on untreated lots (%).

| | 5-ALA conc. (ppm) | | | | | Sun-Catch TM (choline chloride; ppm) |
|---|---|---|---|---|---|---|
| | 0 | 10 | 30 | 100 | 300 | 1,000 |
| Yield (g/section) | 3391 (100) | 3364 (99) | 4648 (137) | 3590 (106) | 3159 (93) | 2617 (77) |
| Average wt. (g/potato) | 231 (100) | 249 (108) | 344 (149) | 248 (107) | 226 (98) | 201 (87) |

As Table 71 clearly shows, treatment with the invention agent increased yield and improved quality.

What is claimed is:

1. A method for promoting the growth of a plant which comprises treating said plant with 1 to 1,000 ppm and 10 to 1,000 l/10 a, in the case of foliage treatment, 1 to 1,000 g/10 a, in the case of soil treatment, or 0.001 to 10 ppm, in the case of soaking treatment, of 5-aminolevulinic acid or a salt thereof.

2. A method for promoting the rooting of a plant which comprises treating said plant with 1 to 1,000 ppm and 10 to 1,000 l/10 a, in the case of foliage treatment, 1 to 1,000 g/10 a, in the case of soil treatment or 0.001 to 10 ppm, in the case of soaking treatment, from 1 hour to 1 week of 5-aminolevulinic acid or a salt thereof.

3. A method for promoting the rooting ratio of a plant which comprises treating said plant with 1 to 1,000 ppm and 10 to 1,000 l/10 a, in the case of foliage treatment, 1 to 1,000 g/10 a, in the case of soil treatment or 0.001 to 10 ppm, in the case of soaking treatment, from 1 hour to 1 week, of 5-aminolevulinic acid or a salt thereof.

4. A method for growing good seedlings of a plant which comprises treating said plant with 1 to 1,000 ppm and 10 to 1,000 l/10 a, in the case of foliage treatment, 1 to 1,000 g/10 a, in the case of soil treatment, or 0.001 to 10 ppm, in the case of soaking treatment, from 1 hour to 1 week, of 5-aminolevulinic acid or a salt thereof.

5. A method for reducing lodging of a plant which comprises treating said plant with 1 to 1,000 ppm and 10 to 1,000 l/10 a, in the case of foliage treatment, 1 to 1,000 g/10 a, in the case of soil treatment, or 0.001 to 10 ppm in the case of soaking treatment, from 1 hour to 1 week, of 5-aminolevulinic acid or a salt thereof.

6. A method for increasing the yield of a plant which comprises treating said plant with 1 to 1,000 ppm and 10 to 1,000 l/10 a, in the case of foliage treatment, 1 to 1,000 g/10 a, in the case of soil treatment, or 0.001 to 10 ppm in the case of soaking treatment, from 1 hour to 1 week, of 5-aminolevulinic acid or a salt thereof.

7. A method for improving the cold resistance of a plant which comprises treating said plant with 1 to 1,000 ppm and 10 to 1,000 l/10 a, in the case of foliage treatment, 1 to 1,000 g/10 a, in the case of soil treatment, or 0.001 to 10 ppm in the case of soaking treatment, from 1 hour to 1 week, of 5-aminolevulinic acid or a salt thereof.

8. A method for maintaining the freshness of a plant which comprises treating said plant with 1 to 1,000 ppm and 10 to 1,000 l/10 a, in the case of foliage treatment, or 1 to 1,000 g/10 a, in the case of soil treatment, of 5-aminolevulinic acid or a salt thereof.

9. A method for maintaining or improving the green color of a plant which comprises treating said plant with 1 to 1,000 ppm and 10 to 1,000 l/10 a, in the case of foliage treatment, 1 to 1,000 g/10 a, in the case of soil treatment, or 0.001 to 10 ppm, in the case of soaking treatment, from 1 hour to 1 week, of 5-aminolevulinic acid or a salt thereof.

10. A method for relieving chemical damage to a plant which comprises treating said plant with 1 to 1,000 ppm and 10 to 1,000 l/10 a, in the case of foliage treatment, 1 to 1,000 g/10 a, in the case of soil treatment, or 0.001 to 10 ppm in the case of soaking treatment, from 1 hour to 1 week, of 5-aminolevulinic acid or a salt thereof.

11. A method for increasing the number of tillers of a plant which comprises treating said plant with 1 to 1,000 ppm and 10 to 1,000 l/10 a, in the case of foliage treatment, 1 to 1,000 g/10 a, in the case of soil treatment, or 0.001 to 10 ppm in the case of soaking treatment, from 1 hour to 1 week, of 5-aminolevulinic acid or a salt thereof.

12. A method for shortening the time required for the growth of a plant which comprises treating said plant with 1 to 1,000 ppm and 10 to 1,000 l/10 a, in the case of foliage treatment, 1 to 1,000 g/10 a, in the case of soil treatment, or 0.001 to 10 ppm, in the case of soaking treatment, from 1 hour to 1 week, of 5-aminolevulinic acid or a salt thereof.

13. A method for promoting the growth of an organ of a plant which comprises incubating calluses, shoot primordia or hairly roots of said plant in a medium containing 0.001 to 10 ppm of 5-aminolevulinic acid or a salt thereof for 1 hour to 1 week.

14. A method for enhancing the photosynthetic activity of a plant which comprises treating said plant with 1 to 1,000 ppm and 10 to 1,000 l/10 a, in the case of foliage treatment, 1 to 1,000 g/10 a, in the case of soil treatment, or 0.001 to 10 ppm, in the case of soaking treatment, from 1 hour to 1 week, of 5-aminolevulinic acid or a salt thereof.

15. A method for suppressing the respiration of a plant which comprises treating said plant with 1 to 1,000 ppm and 10 to 1,000 l/10 a, in the case of foliage treatment, 1 to 1,000 g/10 a, in the case of soil treatment, or 0.001 to 10 ppm in the case of soaking treatment, from 1 hour to 1 week, of 5-aminolevulinic acid or a salt thereof.

16. A method for enhancing the ability to absorb $CO_2$ of a plant which comprises treating said plant with 1 to 1,000 ppm and 10 to 1,000 1/10 a, in the case of foliage treatment, 1 to 1,000 g/10 a, in the case of soil treatment, or 0.001 to 10 ppm, in the case of soaking treatment, from 1 hour to 1 week, of 5-aminolevulinic acid or a salt thereof.

17. A method for increasing the chlorophyll content of a plant which comprises treating said plant with 1 to 1,000 ppm and 10 to 1,000 1/10 a, in the case of foliage treatment, 1 to 1,000 g/10 a, in the case of soil treatment, or 0.001 to 10 ppm, in the case of soaking treatment, from 1 hour to 1 week, of 5-aminolevulinic acid or a salt thereof.

18. A method as claimed in claim 1, wherein said plant is selected from rice, barley, wheat, corn, sweet potato, lawn grass, radish, cucumber, soybean, adzuki bean, kidney bean, onion, spinach, komatsuna, rape, potato, garlic or tea.

19. A method as claimed in any one of claims 2 to 7 or any one of claims 10 to 17, wherein said plant is selected from rice, barley, wheat or corn.

20. A method as claimed in any one of claims 2 to 17, wherein said plant is selected from beans.

21. A method as claimed in any one of claims 2, 3, 6, 7 and 11 to 17, wherein said plant is selected from potatoes.

22. A method as claimed in any one of claims 2 to 17, wherein the foliage treatment is performed with 10 to 500 ppm of 5-aminolevulinic acid or a salt thereof at 50 to 300 1/10 a, the soil treatment is performed with 10 to 500 g/10 a of 5-aminolevulinic acid or a salt thereof, or the soaking treatment is performed with 0.01 to 5 ppm of 5-aminolevulinic acid or a salt thereof for 3 hours to 1 day.

23. A method as claimed in any one of claims 1 to 17, wherein said salt of 5-aminolevulinic acid comprises one or more compounds selected from among the acid-addition salts hydrochloride, phosphate, nitrate, sulfate, acetate, propionate, butyrate, valerate, citrate, fumarate, maleate or malate and the metal salts sodium, potassium or calcium.

24. A method as claimed in claim 1 for promoting the growth of a plant which comprises treating said plant with one or more compounds selected from other plant growth regulators, sugars, amino acids, organic acids, alcohols, vitamins or minerals in combination with said 5-aminolevulinic acid or a salt thereof.

25. A method as claimed in claim 24, wherein said other plant growth regulator is epibrassinolide or choline chloride.

26. A method as claimed in claim 24, wherein said sugar is glucose or sucrose.

27. A method as claimed in claim 24, wherein said amino acid is selected from among asparagine, glutamine, histidine, tyrosine, glycine, arginine, alanine, tryptophan, methionine, valine, proline, leucine, lysine or isoleucine.

28. A method as claimed in claim 24, wherein said organic acid is selected from among formic acid, acetic acid, propionic acid, butyric acid, valeric acid, oxalic acid, phthalic acid, benzoic acid, lactic acid, citric acid, tartaric acid, malonic acid, malic acid, succinic acid, glycolic acid, glutamic acid, aspartic acid, maleic acid, caproic acid, caprylic acid, myristic acid, stearic acid, palmitic acid, pyruvic acid, $\alpha$-ketoglutaric acid or levulinic acid.

29. A method as claimed in claim 24, wherein said vitamin is selected from among nicotinic acid amide, vitamin $B_6$, vitamin $B_{12}$, vitamin $B_5$, vitamin C, vitamin $B_{13}$, vitamin $B_1$, vitamin $B_3$, vitamin $B_2$, vitamin $K_3$, vitamin A, vitamin $D_2$, vitamin $D_3$, vitamin $K_1$, $\alpha$-tocopherol, $\beta$-tocopherol, $\gamma$-tocopherol, $\delta$-tocopherol, p-hydroxybenzoic acid, biotin, folic acid, nicotinic acid, pantothenic acid or $\alpha$-liponic acid.

* * * * *